US007323337B2

(12) United States Patent
Hanazono et al.

(10) Patent No.: US 7,323,337 B2
(45) Date of Patent: Jan. 29, 2008

(54) GENE TRANSFER INTO PRIMATE EMBRYONIC STEM CELLS USING VSV-G PSEUDOTYPED SIMIAN IMMUNODEFICIENCY VIRUS VECTORS

(75) Inventors: Yutaka Hanazono, Tochigi (JP); Yasuji Ueda, Ibaraki (JP); Yasushi Kondo, Kyoto (JP); Yutaka Suzuki, Hyogo (JP)

(73) Assignees: DNAVEC Research Inc., Ibaraki (JP); Tanabe Seiyaku Co., Ltd., Osaka (JP)

( * ) Notice: Subject to any disclaimer, the term of this patent is extended or adjusted under 35 U.S.C. 154(b) by 0 days.

(21) Appl. No.: 10/479,912

(22) PCT Filed: May 29, 2002

(86) PCT No.: PCT/JP02/05225

§ 371 (c)(1),
(2), (4) Date: Jun. 22, 2004

(87) PCT Pub. No.: WO02/101057

PCT Pub. Date: Dec. 19, 2002

(65) Prior Publication Data
US 2004/0234948 A1 Nov. 25, 2004

(30) Foreign Application Priority Data
Jun. 8, 2001 (JP) .............................. 2001-174696

(51) Int. Cl.
*C12N 15/86* (2006.01)
*C12N 5/00* (2006.01)
*C12N 15/82* (2006.01)
*C12N 5/02* (2006.01)

(52) U.S. Cl. ...................... 435/456; 435/325; 435/366; 435/320.1; 435/375; 435/377

(58) Field of Classification Search ............. 424/199.1; 435/325, 366, 456, 320.1, 375, 377
See application file for complete search history.

(56) References Cited

U.S. PATENT DOCUMENTS

| | | | |
|---|---|---|---|
| 5,162,215 A | 11/1992 | Bosselman et al. | |
| 5,576,201 A | 11/1996 | Mason et al. | |
| 6,323,031 B1 | 11/2001 | Cichutek | |

FOREIGN PATENT DOCUMENTS

JP 2002-159289 A 6/2002

OTHER PUBLICATIONS

Nakajima et al, Human Gene Therapy, 11:1863-1874, 2000.*
Kumar et al, Human Gene Therapy, 12:1893-1905, 2001. Abstract only.*
Gardlik et al, Medical Science Monitor, 11:RA110-RA121, 2005.*
Odorico et al, Stem Cells, 19:193-204, 2001.*
Conley et al, The International Journal of Biochemistry and Cell Biology, 36:555-567, 2004.*
Torii et al. Establishment of the Primate Embryonic Stem Cell Lines form Blastocysts Produced by Intra Cytoplasmic Spem Injection (ICSI) or In Vitro Fertilzation (IVF) Using the Japenese Monkey and Cynomolgus Monkey. Theriogenology. Jan. 2001, vol. 55, abs. 374.*
Guidelines for Human Embryonic Stem Cell Research. National Research Council and Institute of Medicine of the National Academies. The National Academies Press, Washington, DC, 2005.*
Hanazono et al., "Genetic Manipulation of Primate Embryonic and Hematopoietic Stem Cells with Simian Lentivirus Vectors," *Trends Cardiovasc. Med.*, 13(3):106-110, 2003.
Nagata et al., "Efficient Gene Transfer of a Simian Immunodeficiency Viral Vector into Cardiomyocytes Derived from Primate Embryonic Stem Cells," *J. Gene Med.*, 5(11):921-928, 2003.
Pfeifer et al., "Transgenesis by Lentiviral Vectors: Lack of Gene Silencing in Mammalian Embryonic Stem Cells and Preimplantation Embryos," *Proc. Natl. Acad. Sci. USA*, 99(4):2140-2145, 2002.
Suemori et al., "Establishment of Embryonic Stem Cell Lines from Cynomolgus Monkey Blastocysts Produced by IVF or ICSI," *Dev. Dyn.*, 222(2):273-279, 2001.
Amit et al., "Clonally Derived Human Embryonic Stem Cell Lines Maintain Pluripotency and Proliferative Potential For Prolonged Periods of Culture," *Dev. Biol.* 227(2):271-278 (2000).
Reubinoff et al., "Embryonic Stem Cell Lines From Human Blastocysts: Somatic Differentiation In Vitro," *Nat. Biotechnol.* 18(4):399-404 (2000).
Thomson et al., "Embryonic Stem Cell Lines Derived From Human Blastocysts," *Science* 282(5391):1145-1147 (1998).
Thomson and Marshall, "Primate Embryonic Stem Cells," *Curr. Top. Dev. Biol.* 38:133-165 (1998).
Williams et al., "Myeloid Leukaemia Inhibitory Factor Maintains the Developmental Potential of Embryonic Stem Cells," *Nature* 336(6200):684-687 (1988).
Xu et al., "Feeder-Free Growth of Undifferentiated Human Embryonic Stem Cells," *Nat. Biotechnol.* 19(10)971-974 (2001).
Asano et al., "Highly Efficient Gene Transfer into Primate Embryonic Stem Cells with a Simian Lentivirus Vector," *Mol. Ther.* 6:162-168 (2002).
Carpenter et al., "Generation of Neurons and Hepatocyte-Like Cells from Human Embryonic Stem Cells," *Pluripotent Stem Cells: Biology and Applications, Keystone Symposium* Abstract 46 (Feb. 6-11, 2001).

(Continued)

*Primary Examiner*—Deborah Crouch
(74) *Attorney, Agent, or Firm*—Clark & Elbing LLP

(57) ABSTRACT

Highly efficient gene transfer into primate-derived embryonic stem (ES) cells has successfully been achieved by using a simian immunodeficiency virus vector (SIV) pseudotyped with VSV-G protein, which is a surface glycoprotein of vesicular stomatitis virus (VSV) The present invention provides simian immunodeficiency virus vectors for gene transfer to primate ES cells. The method for gene transfer to primate ES cells using the vectors of the present invention is useful in, for example, research into embryology and disease, clinical applications, and experimental models for primates. The method is also useful in assaying and screening for genes and reagents able to enhance the specific differentiation of tissues or cells, and which are useful in preparing desired cells or tissues differentiated from ES cells.

12 Claims, 8 Drawing Sheets

OTHER PUBLICATIONS

Carpenter et al., Summary of Numerical Data Presented in a Slide Presentation Entitled "Generation of Neurons and Hepatocyte-Like Cells from Human Embryonic Stem Cells," at the *Pluripotent Stem Cells: Biology and Applications, Keystone Symposium* (Feb. 2001).

Cherry et al., "Retroviral Expression in Embryonic Stem Cells and Hematopoietic Stem Cells," *Mol. Cell Biol.* 20:7419-7426 (2000).

Donovan, "Pluripotent Stem Cells," *IMSUT Symposium for Stem Cell Biology Proceedings* Abstract 67 (Jun. 22-24, 2000).

Donovan, Summary of Numerical Data Presented in a Slide Presentation Entitled "Pluripotent Stem Cells," at the *IMSUT Symposium for Stem Cell Biology Proceedings* (Jun. 2000).

Donovan and de Miguel, "Pluripotent Embryonic Germ Cell Lines," *Pluripotent Stem Cells: Biology and Applications, Keystone Symposium* Abstract 34 (Feb. 6-11, 2001).

Donovan, Summary of Numerical Data Presented in a Slide Presentation Entitled "Pluripotent Embryonic Germ Cell Lines," at the *Pluripotent Stem Cells: Biology and Applications, Keystone Symposium* (Feb. 2001).

Hamaguchi et al., "Lentivirus Vector Gene Expression during ES Cell-Derived Hematopoietic Development In Vitro," *J. Virol.* 74:10778-10784 (2000).

Hanazono et al., "Highly Efficient Gene Transfer into Cynomolgus Monkey Embryonic Stem Cells with a Simian Lentivirus Vector," *Blood* 98(11 part 1):746a (2001).

Liu et al., "Pseudotransduction of Hepatocytes by Using Concentrated Pseudotyped Vesicular Stomatitis Virus G Glycoprotein (VSV-G)—Moloney Murine Leukemia Virus-Derived Retrovirus Vectors: Comparison of VSV-G and Amphotropic Vectors for Hepatic Gene Transfer," *J. Virol.* 70:2497-2502 (1996).

Mangeot et al., "Development of Minimal Lentivirus Vectors Derived from Simian Immunodeficiency Virus (SIVmac251) and Their Use for Gene Transfer into Human Dendritic Cells," *J. Virol.* 74:8307-8315 (2000).

Nakajima et al., "Development of Novel Simian Immunodeficiency Virus Vectors Carrying a Dual Gene Expression System," *Hum. Gene Ther.* 11:1863-1874 (2000).

Schnell et al., "Development of a Self-Inactivating, Minimal Lentivirus Vector Based on Simian Immunodeficiency Virus," *Hum. Gene Ther.* 11:439-447 (2000).

Thomson et al., "Isolation of a Primate Embryonic Stem Cell Line," *Proc. Natl. Acad. Sci. USA* 92:7844-7848 (1995).

Ma, et al., "High-Level Sustained Transgene Expression in Human Embryonic Stem Cells Using Lentiviral Vectors," Stem Cells 21(1):111-117 (2003).

Gropp, et al., "Stable Genetic Modification of Human Embryonic Stem Cells by Lentiviral Vectors," Molecular Therapy 7(2): 281-287 (2003).

Toneguzzo and Keating, "Stable Expression of Selectable Genes Introduced into Human Hematopoietic Stem Cells by Electric Field-Mediated DNA Transfer," Proc. Natl. Acad. Sci. USA 83(10): 3496-3499 (1986).

Eiges et al., "Establishment of Human Embryonic Stem Cell-Transfected Clones Carrying a Marker for Undifferentiated Cells," Curr. Biol. 11:514-518 (2001).

Pera et al., "Human Embryonic Stem Cells," *J. Cell. Sci.* 113:5-10 (2000).

Prelle et al., "Establishment of Pluripotent Cell Lines from Vertebrate Species—Present Status and Future Prospects," *Cells Tissues Organs* 165:220-236 (1999).

* cited by examiner

GENE TRANSFER INTO PRIMATE EMBRYONIC STEM CELLS USING VSV-G PSEUDOTYPED SIMIAN IMMUNODEFICIENCY VIRUS VECTORS

CROSS REFERENCE TO RELATED APPLICATIONS

This application is the U.S. National Stage of International Application No. PCT/JP02/05225, filed May 29, 2002, which claims the benefit of Japanese patent application 2001-174696 filed Jun. 8, 2001.

TECHNICAL FIELD

The present invention relates to simian immunodeficiency virus vectors for gene transfer into primate embryonic stem cells.

BACKGROUND ART

Embryonic stem cells (hereinafter also referred to as "ES cells") are undifferentiated cells having pluripotency and the ability to replicate autonomously. Furthermore, it has been suggested that ES cells have the ability to repair tissues after injury. Therefore, ES cells are being vigorously studied as being useful in screening therapeutically effective substances for various diseases, and in the field of regeneration medicine. Compared to murine ES cells, simian ES cells are closer to those of humans, and therefore, they are expected to be suitable for use in human disease models.

Genetic engineering of ES cells will be extremely critical to the future application of ES cells in the treatment of various diseases and injuries. To modify ES cell properties such as drug sensitivity, the ability to proliferate and differentiate, and the like, stable gene transfer into the ES cell genome is often required. Retroviral vectors that integrate into the host genome are used routinely to achieve stable gene transfer. This is because, when cells such as ES cells that can proliferate and differentiate are used as targets, vectors will be diluted with each cell division if the introduced gene is not integrated into the genome. However, when using the retroviral vector derived from the Moloney murine leukemia virus (MOMLV), a commonly used gene transfer vector, the efficiency of gene transfer to murine ES cells is low (approximately a few percent), and the level of gene expression decreases with time. Recently, a retroviral vector derived from murine stem cell virus (MSCV) was used to improve the efficiency of gene transfer to murine ES cells (to 50% or higher). However, the problem of reduced gene expression over time has not been solved (Cherry, S. R. et al. Mol. Cell Biol. 20:7419, 2000) Recently, it was shown that the use of the lentivirus vector, another vector which can integrate into the genome, can further improve the efficiency of gene introduction into murine ES cells (to 80% or higher) (Hamaguchi, I. et al. J. Virol. 74:10778, 2000). However, in this report, expression of the introduced gene was only observed for a short time (a few days to about two weeks), and there was no record of long-term expression of the introduced gene.

Murine ES cells were used in all of the above-indicated reports of gene transfer to ES cells. To date, there have been no reports on gene transfer to primate ES cells. However, an academic meeting report indicated that gene transfer to primate ES cells is more difficult than gene transfer to murine ES cells. For example, the efficiency of gene transfer to primate ES cells has been reported to be approximately 1% using MOMLV vector, or approximately 5 to 10% using the MSCV vector (IMSUT Symposium for Stem Cell Biology, Tokyo, Japan 2000; Key Stone Sympoia, Pluripotent Stem Cells: Biology and Applications, Durango, Colo., USA, 2001).

DISCLOSURE OF THE INVENTION

An objective of the present invention is to provide simian immunodeficiency virus vectors for gene transfer to primate ES cells. Gene transfer to primate ES cells using the vectors of the present invention is useful for primate-related (including humans) research into embryology and disease, clinical applications, experimental models, and such. This method is also useful for assaying and screening for genes and reagents which are required for specific differentiation of tissues or cells and which are useful in preparing desired differentiated tissues or cells from ES cells.

The present inventors developed a vector capable of gene transfer into primate ES cells. This vector was used in intensive studies to establish a method for efficiently introducing foreign genes into primate ES cells. As a result, the inventors found that an SIV vector pseudotyped with VSV-G protein, which is a surface glycoprotein of vesicular stomatitis virus (VSV), had the ability to transfer genes into primate ES cells with a significantly high efficiency. The efficiency of gene transfer into simian ES cells by the VSV-G-pseudotyped SIV vector was at least several to ten times greater than that into murine ES cells (FIG. 8). The efficiency of SIV vector-mediated transduction into ES cells increased depending on the multiplicity of infection (MOI). At a high MOI, genes were introduced into almost all of the ES cells (FIG. 5). The introduced genes expressed stably over a long period in Cynomolgus monkey-derived ES cells into which an SIV vector containing a reporter gene ligated downstream of the CMV promoter was introduced. This expression hardly decreased even after two months (FIG. 6).

Thus, the present inventors developed a pseudotyped SIV vector which can transfer genes into primate ES cells and succeeded in establishing a method of gene transfer into primate ES cells using this vector. The present invention relates to simian immunodeficiency virus vectors for gene transfer to primate ES cells, and more specifically to:

(1) a recombinant simian immunodeficiency virus vector pseudotyped with VSV-G and able to introduce a gene into a primate embryonic stem cell, (2) the vector according to (1), wherein the recombinant simian immunodeficiency virus vector is derived from the agm strain, (3) the vector according to (1) or (2), wherein the recombinant simian immunodeficiency virus vector is a self-inactivating vector, (4) the vector according to any one of (1) to (3), wherein the primate belongs to the Old World primates, of the family Cercopithecidae, genus *Macaca*, (5) the vector according to any one of (1) to (4), which carries a foreign gene in an expressible state (6) the vector according to (5), wherein the foreign gene is a gene encoding a protein selected from the group consisting of green fluorescent protein, β-galactosidase, and luciferase, (7) a method for introducing a gene into a primate embryonic stem cell, which comprises the step of contacting the cell with the recombinant simian immunodeficiency virus vector according to any one of (1) to (6), (8) a primate embryonic stem cell into which the recombinant simian immunodeficiency virus vector, according to any one of (1) to (6) has been introduced, (9) a cell yielded by allowing the primate embryonic stem cell according to (8) to proliferate and/or differentiate, and

(10) a method for detecting the effect of an introduced gene on the proliferation or differentiation of ES cells, which comprises the steps of:

(a) introducing the vector, according to any one of (1) to (6) into a primate embryonic stem cell; and (b) detecting the proliferation or differentiation of the embryonic stem cell.

As used herein, the term "viral vector" refers to a viral particle capable of transferring nucleic acid molecules into a host. The term "simian immunodeficiency virus (SIV) vector" refers to a vector having the SIV backbone. The term "having the SIV backbone" means that the nucleic acid molecules in the viral particle which constitutes the vector are based on the SIV genome. For example, one of the SIV vectors of the present invention is a vector in which the nucleic acid molecules in the virus particle comprise the packaging signal sequence derived from the SIV genome. In the present invention, the simian immunodeficiency virus (SIV) includes all SIV strains and subtypes. Isolated SIV strains include, but are not limited to, SIVagm, SIVcpz, SIVmac, SIVmnd, SIVsm, SIVsnm, and SIVsyk. The term "recombinant" viral vector refers to viral vectors constructed using recombinant gene technology. Viral vectors which are constructed using DNA encoding the viral genome and packaging cells are included as recombinant viral vectors.

The term "VSV-G-pseudotyped vector" refers to vectors which include the VSV-G protein, a surface glycoprotein of vesicular stomatitis virus (VSV). The VSV-G protein may be derived from an arbitrary VSV strain. For example, the VSV-G protein includes, but is not limited to, proteins derived from the Indiana serotype strain (J. Virology 39: 519-528 (1981)). Alternatively, the VSV-G protein can be a modified VSV-G protein derived from the original protein by, for example, substituting, deleting, and/or adding one or more amino acids. VSV-G-pseudotyped vectors can be prepared by allowing the VSV-G protein to be present during viral production. Viral particles produced in packaging cells can be pseudotyped with VSV-G by expressing VSV-G in these cells. This can be facilitated by, for example, transfection of a VSV-G expression vector, or induced expression of the VSV-G gene integrated into the host's chromosomal DNA. Since VSV-G protein is present on the membrane as a stable glycoprotein homotrimer, vector particles are hardly destroyed during purification and thus can be concentrated to high concentrations using centrifugation (Yang, Y. et al., Hum Gene Ther: Sep, 6(9), 1203-13, 1995).

The pseudotyped retroviral vector of the present invention may further contain envelope proteins from other viruses. For example, an envelope protein derived from a virus which infects human cells is preferred as such a protein. Such proteins include, but are not limited to, retroviral amphotropic envelope proteins. For example, the envelope protein derived from murine leukemia virus (MuLV) 4070A strain can be used as such a retroviral amphotropic envelope protein. Alternatively, the envelope protein derived from MuMLV 10A1 can also be used (for example, pCL-10A1 (Imgenex) (Naviaux, R. K. et al., J. Virol. 70: 5701-5705 (1996)). Also included are proteins from the herpes virus family, such as the gB, gD, gH, and gp85 proteins derived from the herpes simplex virus, and the gp350 and gp220 proteins from the EB virus. Proteins from the Hepadna virus family may include the S protein of hepatitis B virus.

The simian immunodeficiency virus (SIV) was discovered as a monkey-derived HIV-like virus. Along with HIV, SIV forms the primate lentivirus group (E. Ido and M. Hayamizu, "Gene, Infection and Pathogenicity of Simian Immunodeficiency Virus", Protein, Nucleic acid and Enzyme, Vol. 39, No. 8, 1994). This group is further divided into four subgroups: (1) The HIV-1 subgroup, containing HIV-1, the virus which causes human acquired immune deficiency syndrome (AIDS), and SIVcpz, which has been isolated from chimpanzees; (2) the HIV-2 subgroup, containing SIVsmm isolated from Sooty Mangabeys (*Cercocebus atys*), SIVmac isolated from rhesus monkeys (*Macaca mulatta*), and HIV-2, which is less pathogenic in humans (Jaffar, S. et al., J. Acquir. Immune Defic. Syndr. Hum. Retrovirol., 16(5), 327-32, 1997); (3) the SIVagm subgroup, represented by SIVagm isolated from African green monkeys (*Cercopithecus aethiops*); and (4) the SIVmnd subgroup, represented by SIVmnd isolated from Mandrills (*Papio sphinx*).

There are no reports of SIVagm and SIVmnd pathogenicity in natural hosts (Ohta, Y. et al., Int. J. Cancer, 15, 41(1), 115-22, 1988; Miura, T. et al., J. Med. Primatol., 18(3-4), 255-9, 1989; M. Hayamizu, Nippon Rinsho, 47, 1, 1989). In particular, reports of infection experiments suggest that the TYO-1 strain of the SIVagm virus, which is used in the present Examples, is not pathogenic to crab-eating monkeys (*Macaca facicularis*) and rhesus monkeys (*Macaca mulatta*), in addition to its natural hosts (Ali, M. et al, Gene Therapy, 1(6), 367-84, 1994; Honjo, Setal., J. Med. Primatol., 19(1), 9-20, 1990). There are no reports of SIVagm infection, pathogenesis or pathogenic activity in humans. In general, primate lentiviruses have strict species-specificity, and there are few reports of cross-species infection or pathogenesis from natural hosts. Where cross-species infection does occur, the frequency of disease onset is normally low, and the disease progress is slow (Novembre, F. J. et al., J. Virol., 71(5), 4086-91, 1997). Accordingly, viral vectors based on SIVagm, and on the SIVagm TYO-1 strain in particular, are thought to be safer than vectors based on HIV-1 or other lentiviruses, and are thus preferred for use in the present invention.

The simian immunodeficiency virus vector of the present invention may contain a portion of a genomic RNA sequence derived from another retrovirus. Also included in the simian immunodeficiency virus vectors of the present invention are vectors comprising a chimeric sequence, resulting from replacing a portion of the simian immunodeficiency virus genome with, for example, a portion of the genomic sequence of another lentivirus, such as the human immunodeficiency virus (HIV), feline immunodeficiency virus (FIV) (Poeschla, E. M. et al., Nature Medicine, 4(3), 354-7, 1998) or caprine arthritis encephalitis virus (CAEV) (Mselli-Lakhal, L. et al., Arch. Virol., 143(4), 681-95, 1998).

In the retroviral vector of the present invention, the LTR (long terminal repeat) may also be modified. The LTR is a retrovirus-specific sequence, which is present at both ends of the viral genome. The 5' LTR serves as a promoter, enhancing proviral mRNA transcription. Thus, it may be possible to enhance mRNA transcription of the gene transfer vector, improve packaging efficiency, and increase vector titer if the portion exhibiting th 5' LTR promoter activity in the gene transfer vector that encodes viral RNA genome packaged into viral particles, is substituted with another promoter having stronger promoter activity. Furthermore, for example, in the case of lentiviruses, viral tat is known to enhance 5' LTR transcription activity, and therefore, substitution of the 5' LTR for a promoter not present on the tat protein will enable the exclusion of tat from the packaging vector. The RNA of viruses which have infected or invaded cells is reverse transcribed and the subsequent, linking of the LTRs at both ends forms a closed circular structure. Then, viral integrase couples with the linkage site and this structure is then integrated into cell chromosomes. The transcribed proviral mRNA is the region ranging from the 5' LTR transcription initiation site to the 3' LTR polyA sequence located downstream. The 5' LTR promoter portion is not packaged in the virus particle. Thus, even if the promoter is replaced with another sequence, the portion integrated into target cell chromosomes is unchanged. Based on the facts described above, substitution of the 5' LTR promoter is thought to provide a safer vector with a higher titer. Thus, substitution of the promoter at the 5' end of a gene transfer vector can increase the titer of a packagable vector.

Safety can be improved by preventing transcription of the full-length vector mRNA in target cells. This is achieved using a self-inactivating vector (SIN vector) prepared by partially eliminating the 3' LTR sequence. The lentivirus provirus invading the target cell chromosomes, has its 5' end bound to the U3 portion of its 3∝ LTR. Thus, following reverse-transcription, transcripts of the gene transfer vector are integrated into target cell chromosomes such that the U3 portion is at the 5' end. From this point begins the transcription of RNA with a structure similar to the gene transfer vector transcripts. If there were lentivirus or related proteins in target cells, it is possible that the transcribed RNA would be re-packaged and infect other cells. There is also a possibility that the 3' LTR promoter might express host genes located adjacent to the 3' end of the viral genome (Rosenberg, N., Jolicoeur, P., Retroviral Pathogenesis. Retroviruses. Cold Spring Harbor Laboratory Press, 475-585, 1997). These are already considered to be problems of retroviral vectors, and the SIN vector was developed as a way of overcoming these problems (Yu, S. F. et al., Proc. Natl. Acad. Sci. USA, 83(10), 3194-8, 1986). When the 3' LTR U3 portion is deleted from a gene transfer vector, target cells lack the promoters of 5' LTR and 3' LTR, preventing the transcription of the full-length viral RNA and host gene. Furthermore, since only the genes of interest are transcribed from endogenous promoters, highly safe vectors capable of high expression can be expected. Such vectors are preferable in the present invention. SIN vectors can be constructed according to methods known in the art, or methods as described in Examples 1 to 4.

One problem encountered in gene therapy using viral vectors that have the LTR sequence in its genome, (including retroviral vectors) is a gradual decrease in expression of the introduced gene. One factor behind this may be that when such a vector is integrated into the host genome, a host mechanism methylates the LTR, suppressing expression of the introduced gene (Challita, P. M. and Kohn, D. B., Proc. Natl. Acad. Sci. USA 91:2567, 1994). One advantage of SIN vectors is that LTR methylation hardly reduces gene expression level. This is because the vector loses most of the LTR sequence upon integration into the host genome. As described in the Examples, an SIN vector, prepared by substituting another promoter sequence for the 3' LTR U3 region of the gene transfer vector, was revealed to maintain a stable expression for more than two months after gene transfer into primate ES cells. Thus, an SIN vector designed to self-inactivate by the modification of the LTR U3 region is especially suitable in the present invention. Specifically, the present invention includes modified vectors in which one or more nucleotides in the 3' LTR U3 region have been substituted, deleted, and/or added. The U3 region may simply be deleted, or another promoter may be inserted into this region. Such promoters include, for example, the CMV promoter, the EF1 promoter, and the CAG promoter.

It is preferable to design the foreign gene encoded by the vector of the present invention in such a way that it can be transcribed by a promoter other than LTR. For example, when the LTR U3 region is replaced with a non-LTR promoter as described above, it is preferable that the modified LTR drives expression of the foreign gene. Alternatively, as shown in the Examples, the expression of a foreign gene can be induced independent of the LTR by placing a non-LTR promoter in a position different to the LTR region, and placing the foreign gene downstream of this position. The present invention showed that an SIV vector in which the expression of a foreign gene is regulated by a non-LTR promoter ensures long-term stable expression of the foreign gene in ES cells. Thus, a vector in which a non-LTR promoter is placed upstream of a foreign gene, and where the foreign gene is transcribed under the control of that promoter, is particularly suitable in the present invention. Such non-LTR promoters include the CMV promoter, EF1 promoter, and CAG promoter. The CMV promoter in particular is preferable. Such a vector is highly effective when constructed based on the SIN vector described above.

A risk that has been pointed out concerning lentivirus vectors such as the HIV vector is that they may produce replicable viral particles if the host genome already has the HIV provirus, and recombination occurs between the foreign vector and the endogenous provirus. This is predicted to become a serious problem in the future, when the HIV vector is used in HIV patients. The SIV vector used in the present invention has low sequence homology with HIV, and cannot replicate as a virus because 80.6% of the virus-derived sequence has been removed from the vector. Thus, this vector does hardly pose this risk and is safer than other lentivirus vectors. The preferred SIV vector of the present invention is a replication-incompetent virus from which 40% or more, more preferably 50% or more, still more preferably 60% or more, even more preferably 70% or more, and most preferably 80% or more of the genomic sequence of the original SIV has been removed.

Retroviruses can be produced by transcribing in host cells gene transfer vector DNA which contains a packaging signal. This allows the formation of virus particles in the presence of gag, pol and envelope proteins. The packaging signal sequence encoded by the gene transfer vector DNA should preferably be sufficient in length to maintain the structure formed by the sequence. However, in order to suppress the frequency of wild-type virus formation, which occurs due to recombination of the vector DNA packaging signal and the packaging vector supplying the gag and pol proteins, it is also necessary to keep sequence overlapping between these vector sequences to a minimum. Therefore, when it comes to the construction of the gene transfer vector DNA, it is preferable to use a sequence which is as short as possible and yet still contains the sequence essential for packaging, to ensure packaging efficiency and safety.

For example, in the case of the SIVagm-derived packaging vector used in the Example, the type of virus from which the signal to be used is derived is limited to SIV, because HIV vectors are not packaged. However, the SIV-derived gene transfer vector is also packagable when an HIV-derived packaging vector is used. Thus, the frequency of recombinant virus formation can be reduced if the vector particles are formed by combining the gene transfer vector and packaging vector, where each vector is derived from a different type of lentivirus. SIV vectors thus produced are also included in vectors of this invention. In such cases, it is preferable to use combinations of primate lentiviruses (for example, HIV and SIV).

In a preferred gene transfer vector DNA, the gag protein has been modified such that it is not expressed. Viral gag protein may be detected by a living body as a foreign substance, and thus as a potential antigen. Alternatively, the protein may affect cellular functions. To prevent gag protein expression, nucleotides downstream of the gag start codon can be added or deleted, introducing modifications which will cause a frameshift. It is also preferable to delete portions of the coding region of the gag protein. The 5' portion of the coding region of the gag protein is known to be essential for virus packaging. Thus, in a gene transfer vector, it is preferable that the coding region for the gag protein is deleted at the C terminus. It is preferable to delete as large a portion of the gag coding region as possible, so long as the deletion does not considerably affect the packaging efficiency. It is also preferable to replace the start codon (ATG) of the gag protein with a codon other than ATG. The replacement codon can be selected appropriately so as not to greatly affect the packaging efficiency. A viral vector can be produced by introducing the constructed gene transfer vector DNA, which comprises the packaging signal, into appropriate packaging cells. The viral vector particles produced can be recovered from, for example, the culture supernatant of packaging cells.

There is no limitation on the type of packaging cell, as long as the cell line is generally used in viral production. When used for human gene therapy, a human- or monkey-derived cell is suitable. Human cell lines that can be used as packaging cells include, for example, 293 cells, 293T cells, 293EBNA cells, SW480 cells, u87MG cells, HOS cells, C8166 cells, MT-4 cells, Molt-4 cells, HeLa cells, HT1080 cells, TE671 cells, etc. Monkey cell lines include, for example, COS1 cells, COS7 cells, CV-1 cells, BMT10 cells, etc.

The type of foreign gene to be inserted into the vector is not limited. Such genes include nucleic acids which encode proteins, and those which do not encode proteins, for example, antisense nucleic acids or ribozymes. The gene may have a natural or an artificially designed sequence. Artificial proteins include the products of fusion with other proteins, dominant-negative proteins (including soluble receptor molecules and membrane-bound dominant negative receptors), truncated cell-adhesion molecules, and soluble cell-surface molecules. In addition, the foreign gene may be a marker gene to assess the efficiency of gene transfer, stability of expression, and so on. Marker genes include genes that encode green fluorescent protein (hereinafter also referred to as "GFP"), β-galactosidase, and luciferase. The GFP-encoding gene is particularly preferable.

The pseudotyped viral vectors of the present invention can be substantially purified. The purification can be achieved using known purification and separation methods, such as filtration, centrifugation, and column purification. For example, a vector can be precipitated and concentrated by filtering a vector solution with a 0.45-μm filter, and then centrifuging it at 42500×g at 4° C. for 90 minutes.

If necessary, the pseudotyped retroviral vector of the present invention can be prepared as a composition by appropriately using desired pharmaceutically acceptable carriers or media in combination. The term "pharmaceutically acceptable carrier" refers to a material that can be administered in conjunction with the vector and does not significantly inhibit vector-mediated gene transfer. Specifically, the vector can be appropriately combined with, for example, sterilized water, physiological saline, culture medium, serum, and phosphate buffered saline (PBS). The vector can also be combined with a stabilizer, biocide, and such. A composition containing a pseudotyped retroviral vector of the present invention is useful as a reagent or pharmaceutical. For example, a composition of the present. invention can be used as a reagent for gene transfer into ES cells, or as a pharmaceutical for gene therapy.

Nucleic acids inserted into a vector of the present invention can be introduced into the ES cells of primates, including humans, by contacting the vector with the ES cells. The present invention relates to a method for introducing a gene into primate ES cells, which comprises the step of contacting the cells with the vector of the present invention. The present invention also relates to the use of the recombinant simian immunodeficiency virus vector, pseudotyped with VSV-G, for gene transfer to primate ES cells. There are no particular limitations as to the type of primate ES cell into which the gene is introduced. For example, the desired simian ES cells can be used. There are about 200 types of monkeys known in the world. Higher primates are broadly categorized into the following two groups:

(1) New World Primates

Marmosets (*Cailithrix jacchus*) are widely known, and used as experimental primates. The development of New World primates and Old World Primates is essentially the same, although the structure of their embryos and placentas does differ.

(2) Old World Primates

Old World primates are closely related to humans. Rhesus monkeys (*Macaca mulatta*) and cynomolgus monkeys (*Macaca fascicularis*) are known to belong to this group. Japanese monkeys (*Macaca fuscata*) belong to the same genus (the genus *Macaca*) as cynomolgus monkeys. The development of Old World primates is quite similar to that of humans.

As used herein, the term "monkey" or "simian" refers to primates, and specifically to New World and Old World primates. There are no limitations as to the type of simian ES cell into which genes are introduced using a vector of the present invention. Such simian ES cells include marmoset ES cells (Thomson, J. A. et al., Biol. Reprod. 55, 254-259, (1996)), rhesus monkey ES cells (Thomson, J. A. et al., Proc. Natl. Acad. Sci. U.S.A. 92, 7844-7848, (1995)), and cynomolgus monkey ES cells (see Examples). Since Old World primates are closely related to humans and their development is similar to that of humans, they can be used as models to reflect human diseases, and as screening systems for therapeutics for various diseases. Thus, it is preferable to use simian ES cells derived from Old World primates, especially monkeys belonging to the genus *Macaca*, such as the Japanese monkey, the rhesus monkey, and the cynomolgus monkey for introduction of a vector of the present invention.

Primate ES cells can be prepared by a known method or according to the method described herein in the Examples. For example, ES cells can be obtained from developing blastocysts (for example, see the pamphlet WO 96/22362). Specifically, ES cells can be established, for example, by culturing blastocyst-derived inner cell masses on feeder cells or with the leukemia inhibitory factor [LIF, also referred to as "differentiation inhibiting factor (DIF)"].

Such feeder cells include primary cultures of fetal fibroblasts from mice after a gestation of 12 to 16 days, cells obtained by treating mouse fetal fibroblast cell lines, such as STO cells, with mitomycin C, X-rays, or the like. Mouse-derived feeder cells can be prepared on a large scale and are thus advantageous in experiments and such. The feeder cells can be prepared, for example, according to the method described below in the Examples. The feeder cells are plated, for example, on gelatin-coated culture containers using MEM (Minimum Essential Medium Eagle). The feeder cells can be plated in culture containers such that they are fully confluent. The MEM medium in the culture container is changed to ES cell culture medium (see Table 3 in Example 6) and the inner cell masses are plated onto the feeder cells.

Genes can be introduced into primate ES cells using a vector of the present invention by using a method that comprises the step of contacting the vector with primate ES cells. Specifically, for example, ES cells into which a gene is to be introduced are plated on culture dishes covered with feeder cells, and then an SIV vector is added. The efficiency of gene transfer can be improved by simultaneously adding polybrene, for example, at a concentration of about 8 µg/ml. Gene transfer can be carried out at an MOI (multiplicity of infection: the number of infectious viral particles per cell) of, for example, 0.1 to 1000, more preferably 1 to 100, yet more preferably 2 to 50 (for example, 5 to 10). Normally, genes can be introduced into most ES cells by a single addition of the vector, without the need for repeat additions. The vector of the present invention has the advantage that it can achieve exceedingly high gene transfer efficiency without RetroNectin™.

In addition, the present invention relates to primate ES cells in which the VSV-G-pseudotyped viral vector of the present invention has been introduced, and the cells yielded through proliferation and/or differentiation of these ES cells. The differentiation of ES cells can be induced by, for example, adding known differentiation/growth factors such as cytokines, or substrates such as extracellular matrices, by co-culturing with other cells, or by transplanting the cells into individuals, (Hitoshi Niwa "ES cell differentiation fate decision mechanism" Protein, Nucleic acid and Enzyme 45: 2047-2055, 2000; Rathjen, P. D. et al., Reprod. Fertil. Dev. 10: 31-47, 1998).

For example, methods for inducing the differentiation of cells derived from extraembryonic tissue include the following:

| | |
|---|---|
| Extraembryonic endoderm: | Formation of embryoid bodies |
| Trophectoderm: | Suppression of Oct-3/4 expression |

Methods for inducing differentiation of cell types derived from undifferentiated cells include the following:

| | |
|---|---|
| Primitive ectoderm: | Formation of embryoid bodies |
| | Culture supernatant of HepG2 |

Methods for inducing differentiation of cells derived from the ectoderm include the following:

| | |
|---|---|
| Neurons: | Formation of embryoid bodies + treatment with retinoic acid |
| | Formation of embryoid bodies + bFGF |
| | Formation of embryoid bodies + treatment with retinoic acid + a selection of Sox2-positive cells |
| Glial cells: | Formation of embryoid bodies + treatment with retinoic acid |
| | Formation of embryoid bodies + bFGF |
| Epithelium cells: | Formation of embryoid bodies |

Methods for inducing differentiation of cells derived from neural crest cells or such include the following:

| | |
|---|---|
| Pigment cells: | Formation of embryoid bodies |
| | OP9 + ST2 + dexamethasone + SOL |
| Steroid-producing cells: | Over-expression of SF1 |

Methods for inducing differentiation of cells derived from the mesoderm include the following:

| | |
|---|---|
| Hematocytes (Hematopoietic stem cells): | Formation of embryoid bodies + IL-3 + IL-6 + feeder cells |
| | OP9 + feeder cells |
| | A selection of flk1-positive cells |
| Vascular endothelial cells: | A selection of flk1-positive cells |
| Osteoclasts: | Formation of embryoid bodies + retinoic acid treatment |
| Cardiac muscle cells: | Formation of embryoid bodies |
| | Formation of embryoid bodies + a selection of αMHC-positive cells |
| Skeletal muscle cells: | Formation of embryoid bodies |
| Smooth muscle cells: | Formation of embryoid bodies |
| | Formation of embryoid bodies + DMSO |
| Adipocytes: | Formation of embryoid bodies + treatment with retinoic acid + insulin + T3 |

Methods for inducing differentiation of cells derived from endoderm include the following:

| | |
|---|---|
| Insulin-producing cells: | Formation of embryoid bodies |

ES cells in which a gene has been introduced using a pseudotyped viral vector of the present invention, and cells, tissues, organs, and such, that have been differentiated from these ES cells, are useful in assays of and in screening for various pharmaceutical agents. For example, gene transfer to primate ES cells can be used to screen for and assess the efficacy of pharmaceutical agents, genes involved in the specific differentiation of tissues or cells, preferably primate-derived tissues or cells, and the like. The present invention provides a method for screening for genes or pharmaceutical agents involved in the specific differentiation of tissues or cells. The present invention provides a method for detecting the effect of an introduced gene on the proliferation or differentiation of ES cells, which comprises the steps of: (a) introducing a vector of the present invention into primate ES cells, and (b) detecting the proliferation or differentiation of these ES cells. The vector can be introduced into ES cells by contacting primate ES cells of interest with a recombinant simian immunodeficiency virus vector of the present invention. The proliferation of ES cells can be tested by a known method including counting the number of cells, or measuring mitochondrial activity using, for example, an MTT assay. The differentiation of ES cells can be detected by testing the expression of known differentiation marker genes, morphological or biochemical assays of cells or tissues, or the like (Satoshi Niwa "ES cell differentiation fate decision mechanism" Protein, Nucleic acid and Enzyme 45: 2047-2055, 2000; Rathjen, P. D. et al., Reprod. Fertil. Dev. 10: 31-47, 1998). The gene transfer vector can contain desired foreign genes whose effects are to be determined. The vector can be used without a foreign gene when determining the effect of introducing the vector itself, for example, when used as a negative control. Genes influencing the proliferation or differentiation of primate ES cells can be assessed or selected by screening using the detection method described above. Such screenings can be achieved by a method which comprises: the same steps (a) and (b) as in the above description of the detection method, followed by step (c) where an introduced gene with the activity of regulating the proliferation or differentiation of ES cells is selected. Such screening methods are also included in the above-described method for detecting the effect of the gene transfer of the present invention.

One example of screening using such a method is screening for genes which differente primate ES cells into functional cells.

When, for example, determining which of genes A, B, C, D, and E is essential for the differentiation of pancreatic β cells from primate ES cells, in what combination these genes are most effective, or in what order they are preferably introduced, a method that simply and efficiently transfers genes into primate ES cells is useful. The vectors of the present invention meet such requirements. For example, after the vectors of the present invention are constructed for the expression of the genes A, B, C, D, and E, the genes are introduced in various combinations or orders into primate ES cells or into cells differentiated from these ES cells. The effect of gene transfer can be assessed by detecting the differentiation of the cells into which the genes have been introduced.

In addition, the vectors of the present invention are useful, for example, in predicting the presence of side effects in gene therapy that comprises introducing a particular gene into a body.

The toxicities and side effects of gene X on each organ or tissue can be roughly estimated by carrying out experiments that comprise introducing gene X into mice or monkeys. However, it is difficult to determine the influence of gene X on the stem cells of each tissue using conventional methods. There is a possibility that gene X may inhibit the differentiation into functional cells of a particular tissue's stem cells. For example, if the gene inhibits the differentiation of hepatic stem cells, then its inhibitory effect is revealed for the first time when a person is affected with hepatitis or undergoes hepatectomy. Thus, hepatic stem cell differentiation is inhibited by gene X, and the desired hepatic regeneration does not proceed; a serious problem. Such problems can not necessarily be predicted from the results of conventional animal experiments. Using a vector of the present invention, gene X can be introduced into primate ES cells with exceedingly high efficiency. The safety of gene X at various stages of differentiation can be assessed by differentiating the gene-introduced ES cells into various tissue stem cells and further into functional cells.

Assays and screenings using vectors of the present invention are useful in, for example, research into embryology and disease, clinical applications, and experimental models involving primates, and humans and monkeys in particular. The vector of the present invention also enables screening for genes and reagents useful in preparing desired differentiated cells or tissues.

In the screening method described above, the specific differentiation of ES cells into desired tissues or cells can be assessed by, for example, using the expression of a marker specific to the desired tissue or cell type as an index. This marker includes tissue- or cell-specific antigens. For example, markers for neural progenitor cells include nestin, which is an intermediate filament. The marker can be detected by applying an antibody against that specific marker in conventional ELISA, immuno-staining, or such. The marker can also be detected by applying a nucleic acid encoding the marker in conventional RT-PCR, DNA array hybridization, or such. The term "nucleic acid" refers to genomic DNA, RNA, mRNA, cDNA, and such. Genes and reagents obtained by the screening method are included in the present invention.

Furthermore, ES cells in which a pseudotyped retroviral vector of the present invention has been introduced, and cells and tissues differentiated from those ES cells, are also included in the present invention. Such differentiated cells and differentiated tissues can be identified by examining the expression of the above-mentioned marker specific to a tissue or cell type, or through morphological observations of the tissues or cells.

The viral vector of the present invention can be used in gene therapy for any primate genetic disease. There is no limitation as to the type of disease to be treated. For example, diseases to be treated and their single causative genes include: Gaucher disease (β-cerebrosidase (chromosome 20)); hemophilia (blood coagulation factor VIII (X chromosome) and blood coagulation factor IX (X chromosome)); adenosine deaminase deficiency (adenosine deaminase); phenylketonuria (phenylalanine hydroxylase (chromosome 12)); Duchenne muscular dystrophy (dystrophin (X chromosome)); familial hypercholesterolemia (LDL receptor (chromosome 19)); and cystic fibrosis (chromosomal translocation of the CFTR gene). Target diseases in which multiple genes are thought to be involved include neurodegenerative diseases such as Alzheimer's disease and Parkinson's disease, ischemic encephalopathy, dementia, and intractable infections such as AIDS.

In addition, cells, tissues and organs differentiated from gene-introduced ES cells can be used in treating diseases. For example, a disease caused by a gene deficiency or lack can be treated by compensating for the deficient gene by integrating that gene into the chromosome of primate ES cells, and transplanting the cells into a body, thus making up for a shortage of an enzyme, growth factor, or such in the circulating blood. Gene therapy associated with organ transplantation can be undertaken by replacing the histocompatibility antigen of the non-human animal donor with that of a human. In this way, the success rate of xenografts can be improved.

When the ES cells into which a gene has been introduced using a vector of this invention are monkey-derived, the ES cells can be transplanted into disease model monkeys, providing useful models for human disease treatment. Many disease model monkeys are known for various human diseases. For example, model monkeys for human Parkinson's disease can be produced artificially; many naturally diabetic monkeys are bred as accurate models of human diabetes; and SIV infection in monkeys is well known to serve as an accurate model of HIV infection in humans. For such diseases, a system where simian ES cells are transplanted to disease model monkeys as a preclinical test, prior to the clinical application of human ES cells, is exceedingly useful.

Top panel: Observation under a fluorescent microscope of ES cells 21 days (day 21) after gene transfer. CMK-1 cells emitting EGFP fluorescence stand out as islets.

Bottom panel: Observation under a fluorescent microscope of ES cells 62 days (day 62) after gene transfer. CMK-1 cells still emitting EGFP fluorescence stand out as islets.

Figure 8:
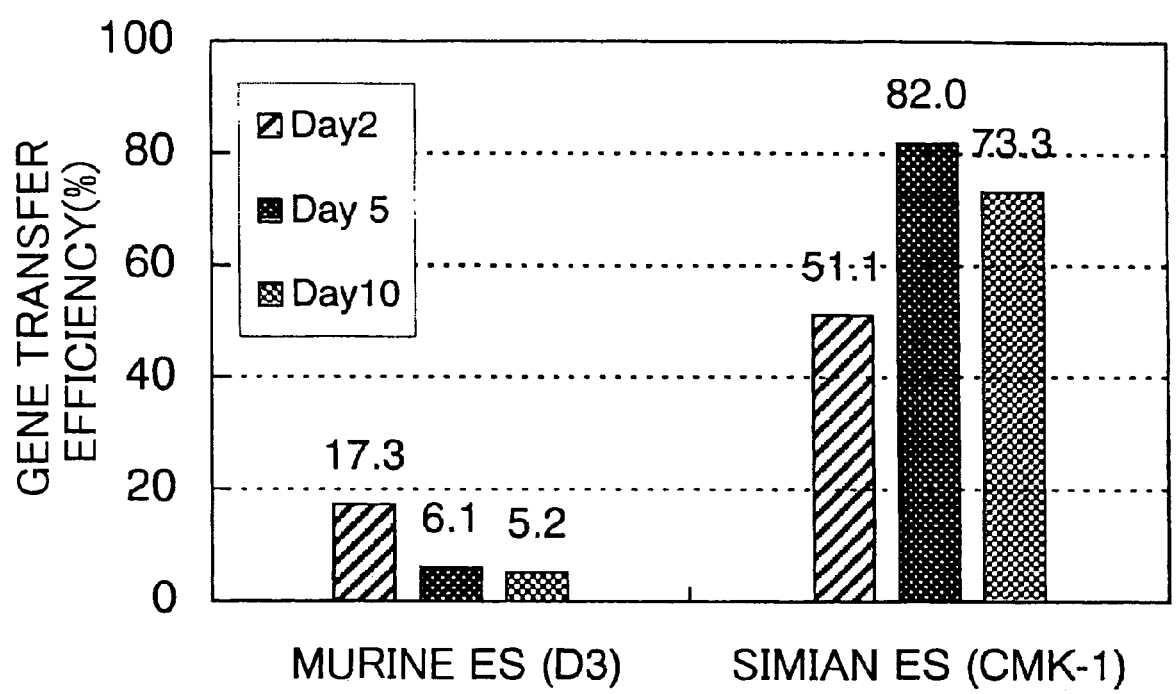

FIG. 8 is a diagram indicating the efficiencies of SIV vector-mediated gene transfer into murine ES cells and simian ES cells (CMK-1 strain). The vertical axis indicates the efficiency (%) of gene transfer into ES cells, normalized for the contribution of feeder cell contamination. Gene transfer into simian ES cells was more efficient than that into murine ES cells. When an SIV-based vector is used, it is predicted that cells from primates, such as SIV's natural host monkeys, will allow for more efficient gene transfer than cells from other species, such as murine cells.

BEST MODE FOR CARRYING OUT THE INVENTION

The present invention is illustrated in detail below with reference to Examples, but it should not be construed as being limited thereto. All of the literature cited throughout this specification is incorporated herein by reference.

EXAMPLE 1

Generation of SIV Vectors

Figure 1:
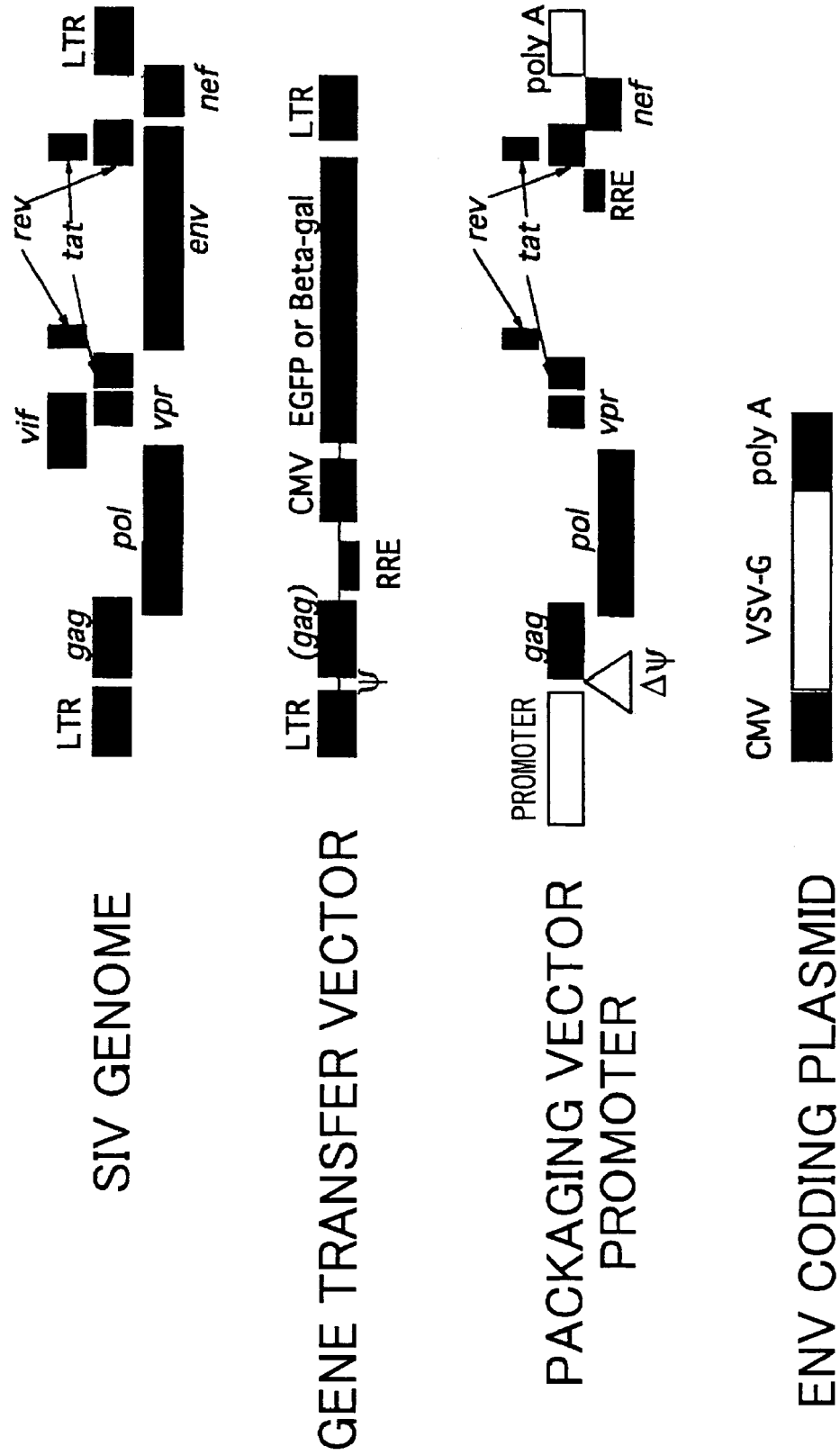
FIG. 1 is a diagram showing an outline of a lentivirus vector system which uses the monkey immunodeficiency virus clone SIVagmTYO1.

SIVagmTYO1 comprising a clone of an African green monkey-derived nonpathogenic immunodeficiency virus was used in the generation of a vector system. FIG. 1 shows the outline of the vector system. All nucleotide numbers are indicated below, with the transcription initiation site of the viral RNA as +1. pSA212 in which SIVagmTYO1 had been inserted was used as a plasmid (J. Viol., vol. 64, pp307-312, 1990). All ligation reactions were carried out using Ligation High (Toyobo) according to the attached instructions.

a. Generation of a Packaging Vector

First, a DNA fragment corresponding to the region (5337-5770) containing vif and the first exon of tat/rev was obtained by PCR, using pSA212 as a template, and using primers 1F (SEQ ID NO: 1) and 1R (SEQ ID NO: 2). A DNA fragment with an EcoRI site at its 3' end was prepared by designing a PCR primer with an EcoRI restriction enzyme site. After digestion with BglII and EcoRI, the PCR fragments were purified using agarose gel electrophoresis and the Wizard PCR Preps DNA Purification System (Promega). The DNA fragments resulting from the above procedure, together with a DNA fragment encoding the gag/pol region (including the region from the XhoI site (356) to the BglII site (5338)), were ligated at the XhoI-EcoRI site of pBluescript KS+ (Stratagene). Then, PCR amplification was performed for a DNA fragment corresponding to the region containing the Rev responsive element (RRE) and the second exon (6964-7993) of tat/rev. In a similar manner as for the PCR fragment described above, PCR was carried out using pSA212 as a template and using primers 2F (SEQ ID NO: 3) and 2R (SEQ ID NO: 4) to add a NotI site at the 3' end. After digestion with EcoRI and NotI, the DNA fragment was purified and inserted at the EcoRI-NotI site of pBluescript KS+ into which gag-tat/rev had been inserted.

DNA fragments containing a splicing donor (SD) site were synthesized (sequence 3F (SEQ ID NO: 5) and 3R (SEQ ID NO: 6)). At the time of synthesis, an XhoI site and an SalI site were integrated into the DNA at the 5' and 3' ends respectively, and then the DNA was inserted at the XhoI site of the above-mentioned pBluescript KS+, into which gag-RRE-tat/rev had been inserted. The resulting plasmid was digested with XhoI and NotI, and the fragment containing the region from SD to tat/rev was purified. The fragment was then inserted at the XhoI-NotI site of a plasmid into which an XhoI/NotI linker (sequence 4F (SEQ ID NO: 7) and 4R (SEQ ID NO: 8)) had been inserted at the EcoRI site of pCAGGS (Gene, vol. 108, pp193-200, 1991). The plasmid obtained via the above method was used as a packaging vector (pCAGGS/SIVagm gag-tat/rev).

b. Generation of Gene Transfer Vectors

PCR was conducted using pSA212 as a template, and using the following primers: primers 5-1F (SEQ ID NO: 9) and 5-1R (SEQ ID NO: 10) to amplify the SIVagmTYO1-derived 5' LTR region (8547-9053+1-982, including a KpnI site at the 5' end, and an EcoRI site at the 3' end); primers 5-2F (SEQ ID NO: 11) and 5-2R (SEQ ID NO: 12) to amplify the RRE (7380-7993, including an EcoRI site at the 5' end, and a SacII site at the 3' end); and primers 5-3F (SEQ ID NO: 13) and 5-3R (SEQ ID NO: 14) to amplify the 3'LTR (8521-9170, including NotI and BamHI sites at the 5' end, and a SacI site at the 3' end). Furthermore, PCR was conducted using pEGFPC2 as a template, and using primers 6F (SEQ ID NO: 15) and 6R (SEQ ID NO: 16) to amplify pEGFPC2-derived (Clontech) CMV promoter and the region encoding enhanced green fluorescent protein (hereinafter also referred to as EGFP) (1-1330; including a SacII site at the 5' end, and a translational stop codon, a NotI site and a BamHI site at the 3' end). The four types of PCR fragments respectively were digested with pairs of restriction enzymes: KpnI and EcoRI, EcoRI and SacII, BamHI and SacI, and SacII and BamHI, and then purified. They were then ligated between the KpnI-SacI site of pBluescript KS+in the following order: 5'LTR→3'→LTR→RRE and CMV promoter. EGFP (pBS/5'LTR.U3G2/RREc/s/CM-VFEGFP/WT3'LTR). In order to insert the β-galactosidase gene used as a reporter gene, DNA fragments containing the 5'LTR region and 3' LTR region respectively were prepared using PCR as described above. After restriction enzyme digestion with both KpnI and EcoRI, and both NotI and SacI respectively, the DNA fragments were purified, and then inserted into the pBluescript KS+ at the KpnI-EcoRI site and the NotI-SacI site respectively (pBS/5'LTR.U3G2/WT3'LTR). A NotI fragment containing the region encoding pCMV-beta β-galactosidase (Clontech) (820-4294) was inserted into the plasmid at the NotI site (pBS/5' LTR.U3G2/beta-gal/WT3' LTR). Then, an RRE sequence (6964-8177; including an EcoRI site at the 5' end and a NotI site at the 3' end), which had been amplified by PCR using pSA212 as a template and using primers 7-1F (SEQ ID NO: 17) and 7-1R (SEQ ID NO: 18), was inserted at the EcoRI-NotI site of plasmid pBS/5' LTR.U3G2/beta-gal/WT3' LTR (pBS/5' LTR.U3G2/RRE6/tr/beta-gal/WT3' LTR). The RRE sequence was cut out with EcoRI and NheI prior to the insertion of the RRE sequence (7380-7993; including an EcoRI site at the 5' end and a NheI site at the 3' end) which had been amplified by PCR using pSA212 as a template and using primers 7-2F (SEQ ID NO: 19) and 7-2R (SEQ ID NO: 20). After the resulting plasmid (pBS/5' LTR.U3G2/RREc/s/beta-gal/WT3' LTR) was digested with NheI and SmaI and blunt ended, a CMV promoter region (8-592; blunt ended AseI-NheI fragment) derived from pEGFPN2 (Clontech) was inserted therein (pBS/5' LTR.U3G2/RREc/s/CM-VFbeta-gal/WT3' LTR). All blunting reactions were performed using a Blunting High (Toyobo) according to the attached instructions. The plasmids pBS/5' LTR.U3G2/RREc/s/CMVFEGFP/WT3' LTR and pBS/5' LTR.U3G2/RREc/s/CMVFbeta-gal/WT3' LTR were digested with KpnI and SacI respectively to provide DNA fragments containing the region between the 5' LTR and the 3' LTR. The fragments were inserted into the pGL3 Control vector (Promega) at the KpnI-SacI site for use as a gene transfer vector (pGL3C/5'LTR.U3G2/RREc/s/CMVFbeta-gal/WT3'LTR or pGL3C/5'LTR.U3G2/RREc/s/CMVFEGFP/WT3'LTR).

EXAMPLE 2

Modification of 5'LTR

Figure 2:
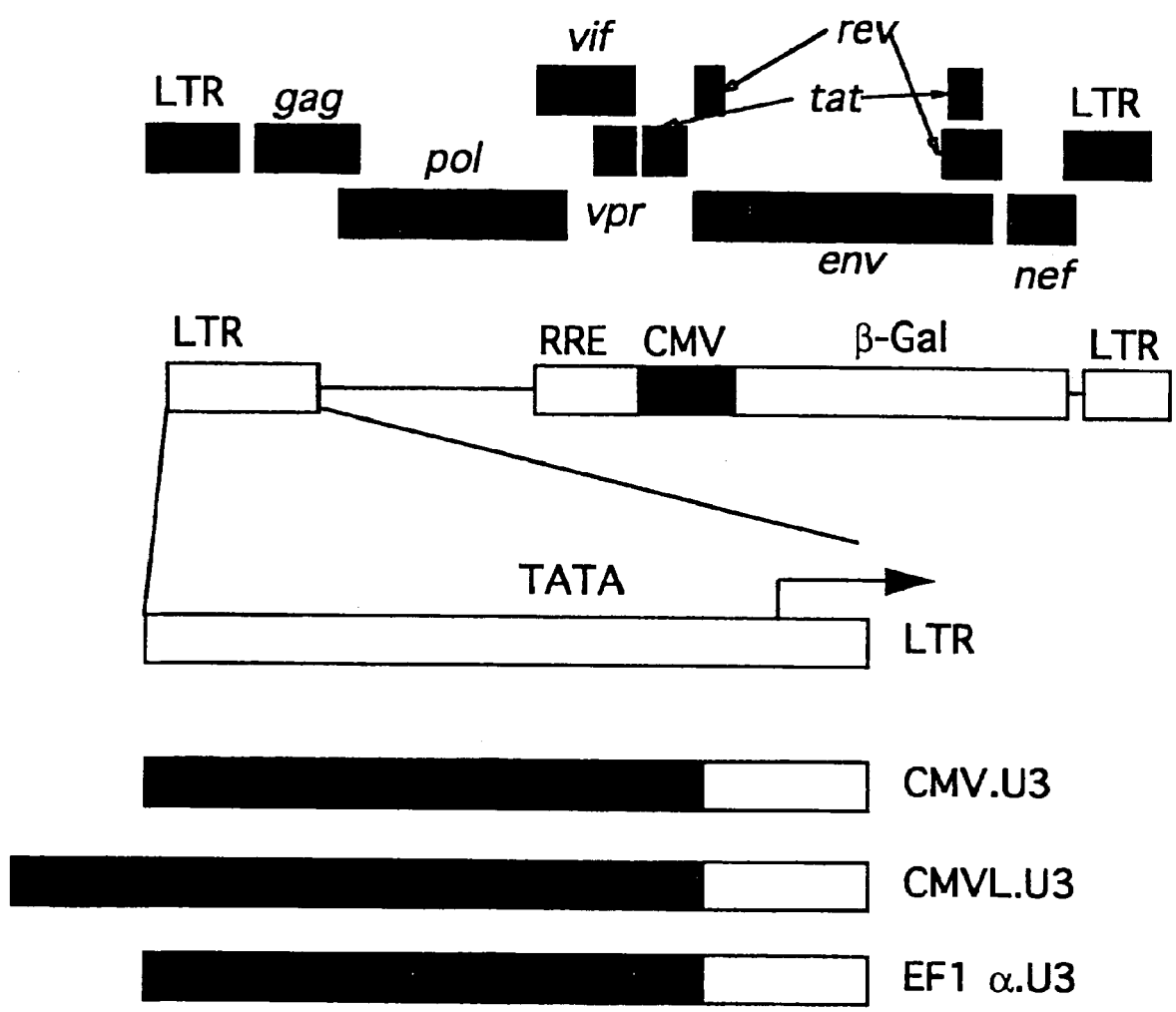
FIG. 2 is a diagram showing the structure of the SIVagm gene transfer vector in which the U3 region, a promoter sequence of 5' LTR, has been substituted with another promoter sequence.

The transcriptional activity of 5'LTR from lentivirus generally depends on the presence of Tat protein, which is a virus-derived factor. Thus, to eliminate Tat dependence as well as to enhance vector titer by replacement with a promoter sequence with stronger transcriptional activity, an SIVagm gene transfer vector was generated. In this SIVagm gene transfer vector, the U3 region, a promoter sequence of the 5'LTR, was replaced with another promoter sequence (FIG. 2).

The replacement of the 5'LTR with a chimeric promoter was achieved as follows. A fragment containing the region downstream of the TATA box on the 5'LTR through to the gag region (9039-9170+1-982) was amplified by PCR using pSA212 as a template and using a series of primers 9-1F to 3F (SEQ ID NOS: 21-23) and primer 9R (SEQ ID NO: 24). Further, fragments containing the CMVL promoter (derived from pCI (Promega); 1-721) were amplified by PCR using pCI as a template and a pair of primers 10-1F (SEQ ID NO: 25) and 10-1R (SEQ ID NO: 26). Fragments containing the CMV promoter (derived from pEGFPN2 (Clontech); 1-568) were amplified by PCR using pEGFPN2 as a template and a pair of primers 10-2F (SEQ ID NO: 27) and 10-2R (SEQ ID NO: 28). Fragments containing the EF1α promoter (nucleotides 2240-2740 from pEF-BOS (Nucleic Acids Research, vol. 18, p5322, 1990)) were amplified by PCR using pEF-BOS as a template and a pair of primers 10-3F (SEQ ID NO: 29) and 10-3R(SEQ ID NO: 30). Fragments containing the CA promoter (nucleotides 5-650 from pCAGGS) were amplified by PCR using pCAGGS as a template and a pair of primers 10-4F(SEQ ID NO: 31) and 10-4R (SEQ ID NO: 32). After amplification, fragments containing the 5 'LTR were mixed with each of the above fragments which each contained a promoter. The primer (10-1F(SEQ ID NO: 25), 10-2F (SEQ ID NO: 27), 10-3F (SEQ ID NO: 29), or 10-4F (SEQ ID NO: 31)) corresponding to the 5' end of each promoter, and the primer corresponding to the 3' end of the 5'LTR (9R) were added thereto. PCR was then performed for another ten cycles to obtain DNA fragments of a chimeric promoter which consisted of each of the four types of promoters and the 5'LTR. The resulting DNA fragments were inserted into a gene transfer vector (PGL3C/5' LTR.U3G2/RREc/s/CMVFbeta-gal/WT3' LTR) at the KpnI-EcoRI site (pGL3C/CMVL.U3G2/RREc/s/CMVFbeta-gal/WT3' LTR, pGL3C/CMV.U3G2/RREc/s/CMVFbeta-gal/WT3' LTR, pGL3C/EF1α. U3G2/RREc/s/CMVFbeta-gal/WT3' LTR, pGL3C/CAG.U3G2/RREc/s/CMVFbeta-gal/WT3' LTR).

EXAMPLE 3

Modification of the 3' LTR

Figure 3:
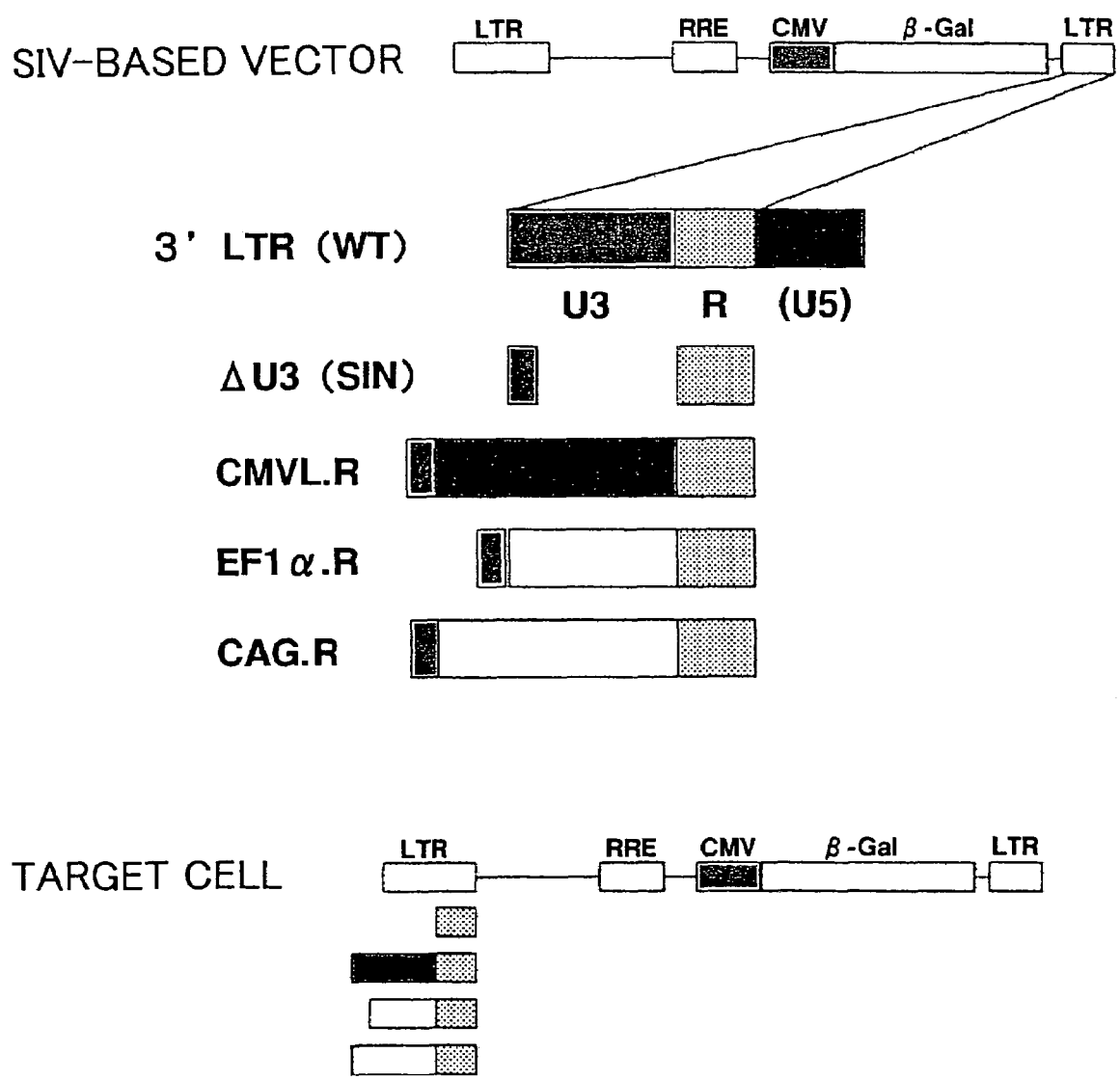
FIG. 3 is a diagram showing the structure of the SIVagm gene transfer vector, in which the U3 region of 3' LTR has been substituted with another promoter sequence. It also shows the structure of the U3 promoter region of the 5' LTR expected to be produced as a result of reverse transcription of the vector in target cells.

A self-inactivating (SIN) vector was constructed by removing a portion from the 3' LTR sequence such that transcription of full-length vector mRNA in target cells was prevented, and safety was improved. In lentivirus vectors it has been demonstrated that the U3 region, which serves as a promoter sequence in the 3' LTR, can be integrated into the 5' LTR U3 promoter region when reverse-transcribed in target cells. Therefore the 3' LTR U3 region of the gene transfer vector plasmid can serve as the 5' LTR U3 promoter involved in gene expression in the genome of target cells (FIG. 3). Thus, a vector was prepared in which the 3' LTR U3 region of the SIVagm gene transfer vector was replaced with another promoter sequence (FIG. 3). In addition, in order to test whether the 5' LTR promoter sequence can be deleted in target cells, a vector in which the 3' LTR U3 region of the SIVagm gene transfer vector had been deleted was also prepared.

The modification and deletion of the U3 promoter sequence of the 3'LTR was achieved as follows. A DNA fragment without the 3'LTR U3 was amplified by PCR using pSA212 as a template and using primers 11F (SEQ ID NO: 33) and 11R (SEQ ID NO: 34). Further, 3'LTRs, in which the U3 region had been replaced with another promoter, were amplified by PCR using a series of primers 12-1F to 3F (SEQ ID NOS: 35-37) and primer 12R (SEQ ID NO: 38), as well as using as templates, each of vector plasmids, obtained by the method described in Example 2, into which a chimeric promoter had been inserted:
pGL3C/CMVL.U3G2/RREc/s/CMVFbeta-gal/WT3' LTR, pGL3C/EF1α.
U3G2/RREc/s/CMVFbeta-gal/WT3' LTR, and
pGL3C/CAG.U3G2/RREc/s/CMVFbeta-gal/WT3' LTR.
The resulting DNA fragments provided by PCR were digested with SalI and SacI, purified, and inserted into pGL3C/CMVL.U3G2/RREc/s/CMVFbeta-gal/WT3' LTR at the SalI-SacI site
(pGL3C/CMVL.U3G2/RREc/s/CMVFbeta-gal/ 3'LTRdeltaU3,
pGL3C/CMVL.U3G2/RREc/s/CMVFbeta-gal/CMVL.R,
pGL3C/CMVL.U3G2/RREc/s/CMVFbeta-gal/EF1α. R, and
pGL3C/CMVL.U3G2/RREc/s/CMVFbeta-gal/CAG.R) respectively.

Figure 4:
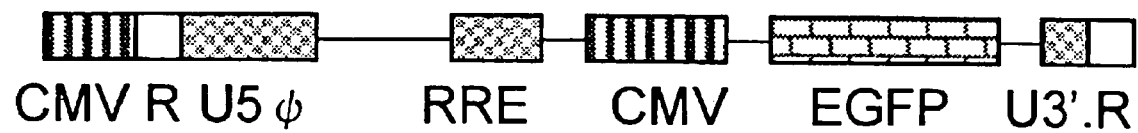
FIG. 4 shows a diagram of the structure of the SIN vector which contains EGFP as a reporter (pGCL3C/CMVL.U3G2/RREc/s/CMVEGFP/3' LTR,,U3) (also abbreviated to "SIN-GFP/SIV" or "SIN CMV EGFP"). The 3' U3 was removed to obtain the self-inactivating vector (SIV vector).

In addition, an SIN vector containing EGFP as a reporter (pGCL3C/CMVL.U3G2/RREc/s/CMVEGFP/3'LTR,,U3) (FIG. 4) was constructed from EcoR1-BamHI-treated pGCL3C/CMVL.U3G2/RREc/s/CMVF β-gal/3'LTR,,U3 by replacing a fragment containing β-gal with the EcoRI-BamHI fragment of the product obtained by PCR using pEGFP-C2 (Clontech) as a template, and the primers EGFPFG2Eco (ATCGGAATTCGGCCGCCATGGTGAG-CAAGGGCGAGGAGCT/SEQ ID NO: 39) and EGFPR-stoNB (CGGGATCCGCGGCCGCTTACTTGTA-CAGCTCGTCCATGCC/SEQ ID NO: 40). This was then inserted into the EcoRI-SacII site of the EcoRI-SacII fragment of the PCR product amplified by using pSA212 as a template, and the primers 5-2F (SEQ ID NO: 11) and 5-2R (SEQ ID NO: 12).

EXAMPLE 4

Preparation of SIV on a Large Scale

Transfection

Cells from the cell line 293T, derived from human fetal kidney cells, (Proc. Natl. Acad. Sci. USA, vol. 90, pp8392-8396, 1993) were plated in fifty 15-cm dishes at a cell density of $2.5 \times 10^6$ cells/dish, and cultured for 48 hours in DMEM (GibcoBRL) containing 10% inactivated fetal calf serum (FCS). Twenty ml of medium was used per 15-cm dish. After the cells had been cultured for two days, 300 μg. of the gene transfer vector pGCL3C/CMVL.U3G2/RREc/s/CMVEGFP/3'LTR,,U3, 150 μg of the packaging vector pCAGGS/SIVagm gag-tat/rev, and 50 μg of the VSV-G (pVSV-G) expression vector were dissolved in 75 ml of OPTI-MEM (Invitrogen) Then 2 ml of PLUS reagent (Invitrogen) was added to the solution. After stirring, the solution was allowed to stand at room temperature for 15 minutes. Three ml of LIPOFECTAMINE (Invitrogen) was separately mixed with 75 ml of OPTI-MEM, and then combined with the DNA mixture described above. The resulting mixture was allowed to stand at room temperature for 15 minutes.

A 3-ml aliquot of this solution was added dropwise to each 293T cell culture in which the medium had been replaced with 10 ml of OPTI-MEM. The cells were incubated under 10% $CO_2$ at 37° C. for three hours. Ten ml of DMEM containing 20% FCS was added to each dish, and the cells were cultured for a further 21 hours. 24 hours after transfection, the medium of each dish was replaced with 20 ml of DMEM containing 10% FCS. The cells were cultured for a further 24 hours.

Recovery and Concentration of Vectors

The culture supernatant was saved and filtered with a 0.45-μm filter, followed by centrifugation at 42500 g and 4° C. for 90 minutes. The resulting pellet was dissolved in 10 ml of TBS containing 10 mM $MgCl_2$, 3 mM spermine, 0.3 mM spermidine, and 100 μM dNTP, and then the solution was incubated at 37° C. for two hours. The sample was then centrifuged at 42500 g and 4° C. for two hours. The resulting pellet was suspended in 1 ml of PBS containing 5% FCS and 2 μg/ml polybrene, and then frozen and stored at −80° C.

EXAMPLE 5

Preparation of Simian Blastocysts

In order to obtain blastocysts suitable for establishing ES cells, fertilization was achieved using in-vitro fertilization and sperm microinjection. The fertilized eggs were then manipulated for blastocyst development using the in-vitro culture method.

(1) Ovary Stimulation Method 1.8 mg of gonadotropin-releasing hormone (GnRH) [(Trade name: Leuplin (Takeda Chemical Industries, Ltd.; or Trade name: Sprecur (Hoechst Marion Roussel)] was given subcutaneously to female cynomolgus monkeys (four to 15 years old). Two weeks after GnRH administration, the hormones indicated below were administered intramuscularly once a day at regular times (in the evening in this Example) for nine consecutive days. These hormones were: pregnant mare serum gonadotropin (PMSG) [Trade name: Serotropin (Teikoku Hormone Mfg. Co., Ltd.)] at a dose of 25 IU/kg; and human menopausal gonadotropin (hMG) [Pergonal (Teikoku Hormone Mfg. Co., Ltd.) at a dose of 10 IU/kg; or follicle stimulating hormone (FSH) [Fertinorm (Serono Laboratories)] at a dose of 3 IU/kg. After five days of administration, the growth of ovarian follicles was confirmed by observation of ovaries using a laparoscope (external diameter=3 mm).

After the monkeys had been administered with PMSG, hMG, or FSH and the ovarian follicles had been confirmed to have grown sufficiently, human chorionic gonadotropin (hCG) [Trade name: Puberogen (Sankyo CO., Ltd.)] was administered intramuscularly a single time and at a dose of 400 IU/kg. Eggs were collected 40 hours after hCG administration.

Egg collection was carried out by aspirating eggs together with follicular fluid by puncturing the ovarian follicles using a 2.5-ml syringe with a 60-mm 19G or 20G Cathelin puncture needle, which contained about 0.5 ml of an α-MEM (α-Modification of Eagle's Medium; ICD Biomedical Inc.) solution containing 10% SSS (Serum Substitute Supplement; Irvine Scientific Sales Inc.). Egg collection was carried out while observing the ovary with a laparoscope (external diameter=10 mm).

Immediately after collection, mature eggs wrapped with cumulus cells were isolated under a stereoscopic microscope, and transferred into TALP containing 0.3% BSA (hereinafter abbreviated as BSA/TALP) The eggs were pre-cultured under 5% $CO_2$, 5% $O_2$, and 90% $N_2$ in a $CO_2$ incubator at 37° C. for three to four hours.

(2) Sperm Collection (i) Method of Collection from the Epididymis

The epididymis was collected from male cynomolgus monkeys (ten to 15 years old) and a 1-ml syringe with a 23G needle was immediately inserted into the seminal duct. BWW containing 0.3% BSA (hereinafter abbreviated as BSA/BWW) was gently injected to the duct. The tail of epididymis was cut and the seminal fluid which flowed from the duct was collected.

(ii) Collection Method Using Electric Stimulation (a) Rectal Method

Male cynomolgus monkeys (ten to 15 years old) were anesthetized using ketamine hydrochloride and xylazine hydrochloride (at doses of 5 mg/kg and 1 mg/kg respectively), and allowed to lie in a supine position. Keratin cream was applied to a rectal bar electrode connected with an electric stimulator, and the electrode was gently inserted into the monkey's rectum. The penis was washed with sterilized physiological saline, and dried with a paper towel or the like. The tip of the penis was inserted into a test tube (50 ml). Then, five volts of AC electric current was introduced using the electric stimulator. The cycle of power on (for three to five seconds) and off (for five seconds) was repeated up to three times. Voltage application was terminated when ejaculation occurred during the cycle. When no ejaculation occurred, the same procedure was carried out using ten volts instead of five volts. If ejaculation still had not occurred, the same procedure was repeated at 15 volts, and likewise at 20 volts.

(b) Penis Method

Without anesthesia, the limbs of male cynomolgus monkeys (ten to 15 years old) were held such that the monkeys were fixed to the front of the cage and the penis could be conveniently reached. With surgical latex gloves, the penis was washed with sterile physiological saline and then dried with paper towel or the like. An electric stimulator was prepared, and electrodes were attached to the penis using clips. First, five volts of DC current was introduced at one-second intervals, and then the intervals were gradually shortened. When no ejaculation occurred, the same procedure was repeated at ten volts, and likewise at fifteen volts, and then at 20 volts. If ejaculation had still not occurred, the same procedure was repeated using AC voltage.

(3) Method of post-treatment and cryopreservation of seminal fluid after collection (Torii, R., Hosoi, Y., Iritani, A., Masuda, Y. and Nigi, H. (1998). Establishment of Routine Cryopreservation of Spermatozoa in the Japanese Monkey (*Macaca fuscata*), Jpn. J. Fertil., 43(2), 125-131).

Seminal fluid collected by the rectal method or the penis method was allowed to stand in a $CO_2$ incubator at 37° C. for about 30 minutes. The liquid components were saved, and about 1 to 2 ml of BWW culture medium (Biggers, Whitten and Wittinghams) containing 0.3% BSA (BSA/BWW) was added to this liquid to prepare a sperm solution. This solution was then gently overlaid onto 2.5 ml of 80% Percoll (American Pharmacia Biotech Inc.), and 2.5 ml of 60% Percoll. The resulting sample was centrifuged at 1,400 rpm at room temperature for 20 minutes, and then the upper layer was removed by aspiration, leaving only about 0.5 ml at the bottom of the test tube. About 10 ml of BSA/BWW was added to the liquid and the resulting mixture was gently mixed. After the mixture was centrifuged at 1,400 rpm at room temperature for three minutes, the upper layer was removed by aspiration, leaving only about 0.5 ml at the bottom.

An appropriate amount of BSA/BWW was added to the collected sperm to adjust the sperm density to about $5 \times 10^7$ to $1.0 \times 10^8$ cells/ml. The resulting sperm solution was allowed to stand at 4° C. for about 60 to 90 minutes. Then, a TTE-G solution [TTE medium (composition of the 100-ml medium: 1.2 g of Tes, 0.2 g of Tris-HCl, 2 g of glucose, 2 g of lactose, 0.2 g of raffinose, 20 ml of egg yolk, 10,000 IU of penicillin-G, 5 mg of streptomycin sulfate) containing glycerol at the final concentration of 12%] having a $\frac{1}{5}^{th}$ of the volume of the sperm solution, was gently dropped into the sperm solution in iced water. The resulting mixture was allowed to stand for five minutes, and then the above-described cycle of dropping the TTE-G solution and standing was repeated five times.

After standing the mixture in iced water for 60 to 90 minutes, the resulting sperm solution was added to a 0.25- or 0.5-ml straw. The straw was held in the upper part of a liquid nitrogen container for about five minutes, and then above the liquid nitrogen surface for five minutes. The straw was then stored in liquid nitrogen.

(4) Preparation of Sperm for In-Vitro Fertilization

Straws removed from liquid nitrogen were incubated at room temperature for 30 seconds, and then incubated in a 37° C. water bath for 30 seconds to thaw the stored sperm solution. Then, 10 ml of BSA/BWW containing 1 mM caffeine (Sigma) and 1 mM dbC-AMP (Sigma) was added to the straw, and the mixture was incubated in a $CO_2$ incubator (5% $CO_2$) at 37° C. for 30 minutes, facilitating sperm capacitation.

The sperm liquid was centrifuged at 1,000 rpm (200×g) for two minutes, and the resulting supernatant was discarded. About 0.5 to 1 ml of BSA/BWW containing 1 mM caffeine and 1 mM dbC-AMP was added to the sperm. The sperm solution was allowed to stand in a $CO_2$ incubator (5% $CO_2$) at 37° C. for 60 minutes. The sperm which swam to the top were collected, and sperm count and motility were examined. Thus, in this way sperm for in-vitro fertilization were prepared.

(5) Fertilization Method (A) In-Vitro Fertilization Method

One to five eggs wrapped with cumulus cells were transferred into 50-µl BSA/BWW spots, which were covered with mineral oil and in a plastic dish. Then, the sperm suspension was transferred into each drop at a density of $5.0 \times 10^5$ to $1.0 \times 10^6$ cells (sperms)/ml. The drops were covered with mineral oil, after which insemination took place.

After fertilization, the eggs were cultured in a $CO_2$ incubator with 5% $CO_2$, 5% $O_2$, and 90% $N_2$ at 37° C. Five hours after insemination, TALP solution was substituted for the BWW solution. Fertilization efficiency was determined to be about 45%, and thus fertilized eggs were yielded with a high efficiency. Eggs in which fertilization was confirmed were cultured for about 20 hours. The eggs were then transferred into a CMRL-1066 solution and further cultured.

The CMRL-1066 solution was prepared as follows: 0.014615 g of L-glutamine (1 mM) was dissolved in 10 ml of solution A [penicillin G (1000 units), 0.5 ml of gentamicin sulfate (10 mg/ml), 10 ml of CMRL-1066 (10×) (without $NaHCO_3$ and L-glutamine), 0.218 g of $NaHCO_3$; 6.7 ml of sodium lactate (290 mOsmol's stock); adjusted to 100 ml with water]. The solution thus prepared was sterilized by filtration. Solution B (10 ml) was prepared by adding 9 ml of solution A to 1 ml of the sterilized solution. Solution C was prepared by dissolving 0.0055 g of sodium pyruvate (final concentration=5 mM) in solution B. 8 ml of solution C was combined with 2 ml of BCS (bovine calf serum). The resulting mixture was sterilized by filtration to prepare CMRL-1066 solution.

(B) Sperm Microinjection
(i) Egg Preparation

The harvested eggs were placed in a 50-µl spot of TALP (BSA/TALP) solution containing 0.3% BSA covered with mineral oil (Sigma), and pre-cultured in 5% $CO_2$, 5% $O_2$, and 90% $N_2$ at 37° C. for about two to four hours.

To confirm egg maturity, the egg culture was incubated for one minute in a TALP-HEPES solution containing 0.1% hyaluronidase (Sigma) Cumulus cells were then removed by pipette. The recovered eggs were categorized under an inverted microscope into the following four classes (Class-1 to -4):

Class-1: mature eggs having polar bodies (PB)
Class-2: eggs in the middle of the maturation process, without PB or germinal vesicles (GV)
Class-3: premature eggs containing GV
Class-4: eggs markedly distorted or with degenerated cytoplasm comprising retrogressive changes Immediately after categorization, Class-1 eggs were used in microscopic fertilization. Class-2 and Class-3 eggs were placed in 50-µl spots of BSA/TALP solution covered with mineral oil, and then further cultured in 5% $CO_2$, 5% $O_2$, and 90% $N_2$ at 37° C. 24 hours after culture, egg maturation was confirmed. Matured eggs were used in microscopic fertilization at this time. The remaining premature eggs and Class-4 eggs were not used in fertilization.

(ii) Sperm Preparation

Sperm were prepared according to the method described in the "In-vitro fertilization method" section.

(iii) Sperm Microinjection

Microscopic fertilization was carried out under an inverted microscope (Olympus IX70) equipped with a micro-manipulator from Narishige.

In a 15-cm dish, spot 1 (15 µl of a diluted sperm solution), spot 2 (3×5 µl of 10% polyvinylpyrrolidone/PBS culture medium [PVP; mean molecular weight=about 360,000 (Nacalai Tesque)], and spot 3 (3×5 µl of TALP-HEPES (BSA at a final concentration of 3 mg/ml) solution for egg manipulation) were placed successively, and the spot surfaces were covered with mineral oil to prevent drying. Microscopic fertilization was performed using this dish. No heating devices were used in this Example, and any temperature changes during manipulation were ignored. However, it is possible to use a heating device.

The injection needle used was that used for microscopic fertilization in humans, and was set to an inclination angle of 30 degrees (external diameter, 7 to 8 µm; internal diameter, 5 to 7 µm (Medi-Con International Co., Ltd. The above-mentioned needle was connected with a high precision Alcatel syringe.

The needle used to hold the egg was the same as that used for microscopic fertilization in humans, and was set to an inclination angle of 30 degrees. Alternatively, a needle (external diameter=about 100 µm; internal diameter at the end=about 15 µm) prepared using a magnetic puller (Trade name: PN-30, Narishige) was used. The above-mentioned needles were connected with Narishige injectors that had a 2000-µl air-tight syringe.

Sperm with a high motility were selected according to the same criteria used for microscopic fertilization in humans, and then aspirated from spot 1. The selected sperm were transferred into spot 2. In spot 2, sperm motility was reduced due to PVP viscosity. To prevent the sperm from moving, the sperm membranes were partially disrupted by rubbing the sperm tails with the injection needle. The sperm were aspirated together with the viscous solution, and then transferred into spot 3.

Matured eggs were placed in spot 3, and then fixed at the 6 or 12 o'clock position using the holding needle, so as not to disrupt the chromosomes under the polar bodies with the injection needle. Then, a sperm was placed at the tip of the injection needle, and inserted into the egg. After confirming that the needle had passed through the zona pellucida, the egg cell membrane was aspirated. Membrane rupture was confirmed, and then the contents of the injection needle (the sperm and egg cytoplasm) were injected into the egg. This procedure of injecting sperm and egg cytoplasm was carried out repeatedly. Two to three eggs were fertilized in a single manipulation. However, if the inner surface of the needle tip became clogged with sperm or egg cytoplasm, the tip was washed with the liquid in spot 2.

The microscopically fertilized eggs were immediately placed in an incubator and cultured in 5% $O_2$, 5% $CO_2$, and 90% $N_2$ at 37° C. Immediately after microscopic fertilization, 50-µl spots of CMRL-1066 solution were created in an uncoated 6-cm culture dish and covered with paraffin oil. The spots were typically equilibrated with a gas. phase for at least three hours. 24 hours after microscopic fertilization, the eggs were transferred from the TALP solution into a spot of the above-mentioned CMRL-1066 solution, and then incubated in 5% $O_2$, 5% $CO_2$, and 90% $N_2$ in a tightly sealed $CO_2$ incubator at 37° C. for eight days. Fertilized eggs were produced with high fertilization efficiency (about 75 to 85%).

(6) Culture Method

Following in-vitro fertilization and microscopic fertilization, eggs confirmed to be fertilized were cultured using hanging microdrop cultures in which the culture medium was covered with mineral oil to avoid abrupt changes in temperature and carbon dioxide concentration. This method has been widely used for experimental animals such as mice and rabbits, but has not been routinely used for humans. The eggs were cultured under air tight conditions to avoid unnecessary stresses caused by temperature and pH changes. Thus, opening and closing of the incubator door was avoided until blastocyst formation was predicted, namely for seven days after the start of the in-vitro fertilization cultures, or for eight days after the start of the microscopic fertilization cultures.

The medium, temperature, and gas phase used for the cultures were as follows:

Culture Medium: TALP & CMRL-1066

The mediums used were BWW, which is routinely used for mice, and P1 (Nakamedical Inc.), Blast medium (Nakamedical Inc.), and the newly developed HFF (human foilcular fluid; Fuso Pharmaceutical Industries, Ltd.), which are used for humans. When cultured in these mediums, egg fertilization and segmentation progressed normally until the development stopped at the morula stage. After confirmation of fertilization, a combination of TALP and CMRL-1066 culture media was applied, and fertilized embryos went on to form blastocysts at an exceedingly high rate of 40 to 46%. The use of the HEPES buffer system TALP instead of PBS, a phosphoric acid buffer system, in manipulations outside the incubator was presumed to reduce adverse effects on the eggs.

Culture Temperature: 38° C.

Mouse and human embryos are routinely cultured at 37° C. However, at this temperature, the eggs only developed slowly and the development stopped at the morula stage. The eggs were then cultured at the slightly higher temperature of 38° C., which is similar to the temperature of 38.5° C. used for culturing bovine embryos, etc. Blastocysts were produced seven days after in-vitro fertilization, and eight days after microscopic fertilization.

Culture Atmosphere: 5% $CO_2$/5% $O_2$/90% $N_2$

Under the typical conditions of 5% $CO_2$ and 95% air, the eggs stopped developing farther than the morula stage. However, when cultured in 5% $CO_2$, 5% $O_2$, and 90% $N_2$, the eggs were revealed to form blastocysts with a high efficiency.

The TALP solution and TALP-HEPES solution were prepared as follows:

TABLE 1

| REAGENT | STOCK SOLUTION (mM) | STOCK SOLUTION (g/100 mol) | FINAL SOLUTION (mM) | STOCK SOLUTION(ml) TALP | STOCK SOLUTION(ml) TALP-HEPES |
|---|---|---|---|---|---|
| HEPES | — | — | 10.0 | — | 240 mg |
| NaCl | 157.0 | 0.92 | 114.0 | to 100 ml | to 100 ml |
| KCl | 166.0 | 1.24 | 3.16 | 1.9 | 1.9 |
| $CaCl_2$ | 120.0 | 1.76 | 2.0 | 1.7 | 1.7 |
| $MgCl_2 \cdot 6H_2O$ | 120.0 | 2.44 | 0.5 | 0.41 | 0.41 |
| SODIUM LACTATE | 150.0 | — | 10.0 | 6.7 | 6.7 |
| WATER | — | — | — | — | 7.1 |
| $NaH_2PO_4 \cdot H_2O$ | 20.5 | — | 0.35 | 1.7 | 1.7 |
| GLUCOSE | 295.0 | 5.31 | 5.0 | | |
| $NaHCO_3$ | 167.0 | 1.40 | 25.0(TALP) 2.0(TALP-HEPES) | 15.0 | 1.2 |

PENICILLIN G(10,000 UNITS/100 ml) AND PHENOL RED (1 mg/100 ml)
STOCK SOLUTIONS ARE AUTOCLAVED AND STORED.

Just prior to preparing the TALP solution, the reagents listed below were prepared and sterilized with filters.

| Sodium pyruvate | 0.5 mM | 0.0055 g (per 100 ml) |
| Gentamicin sulfate (10 mg/ml) | 50 µg/ml | 50 µl |
| BSA | 3 mg/ml | 0.3 g |

Just prior to preparing the TALP-HEPES solution, the reagents listed below were prepared and sterilized with filters:

| Sodium pyruvate | 0.1 mM | 0.0011 g (per 100 ml) |
| BSA | 3 mg/ml | 0.3 g |

When preparing the TALP-HEPES solution, 50 ml of NaCl and Na-HEPES (N-2-hydroxyethyl piperazine-N'-2-ethane sulfonate), phenol red, and penicillin G were first dissolved. The required aliquot of each stock solution was added to the resulting solution, and finally the volume was adjusted to 100 ml using NaCl stock solution. The pH of the resulting solution was adjusted to 7.4 using 1M NaOH. A solution of sodium lactate was prepared by combining a stock solution (60% syrup) with water at the ratio of 1:35. After 1 mg/ml phenol red was added to the resulting solution, the pH of the mixture was adjusted to 7.6 using 1M NaOH, and then sterilized by filtration. The reagent thus prepared can be stored at 4° C. for one week. 28 mg of $NaHPO_4 \cdot H_2O$ was dissolved in 10 ml of glucose solution, and the resulting solution was sterilized by filtration. This solution can also be stored at 4° C. for one week.

The composition of BWW (Biggers, Whitten and Whittingham) solution is shown in Table 2.

TABLE 2

| REAGENT | AMOUNT* (mg) |
|---|---|
| SODIUM CHLORIDE | 2,770 |
| POTASSIUM CHLORIDE | 178 |
| $KH_2PO_4$ | 81 |
| MAGNESIUM SULFATE | 147 |
| $NaHCO_3$ | 1,053 |

TABLE 2-continued

| REAGENT | AMOUNT* (mg) |
|---|---|
| SODIUM PYRUVATE | 14 |
| D(+)-GLUCOSE(ANHYDROUS) | 500 |
| PENICILLIN G | 31 |
| STREPTOMYCIN | 25 |
| DL-SODIUM LACTATE | 1,037 |
| CALCIUM LACTATE | 263 |
| PHENOL RED 1 mg Merk | 1 |

*/500 ml

EXAMPLE 6

Method for Establishing Simian ES Cells (1) Preparation of Feeder Cells

Primary embryonic fibroblast cells (hereinafter also referred to as MEF cells) prepared from 12.5 day-old mouse embryos were cultured from the first to the third generation in MEM containing 10% fetal bovine serum (FBS), until the cells were confluent. To inactivate cell division, MEF cells were then cultured for two or three hours in MEM containing mitomycin C (MMC) at a final concentration of 10 µg/ml. The culture medium containing MMC was removed, and the cells were washed three times with PBS. After washing, the cells were harvested from the culture dish by trypsinization (0.05% trypsin and 1 mM EDTA) and the cell count was determined.

MMC-treated MEF cells were plated at a cell density of $2 \times 10^4$ cells/well into each well of 24-well gelatin-coated culture dishes.

The cells obtained were plated on dishes to confirm that the cell counts were sufficient, and then murine ES cells were cultured on the MEF cells, and cell properties were examined. The MEF cells were revealed to be suitable as feeder cells because the cells had excellent growth capacity and still remained undifferentiated. Cells in the third generation or younger (the first to third generation) were suitable as feeder cells.

(2) Separation of the Inner Cell Mass from Simian Blastocysts

To remove the zona pellucida, simian blastocysts were transferred into M2 culture medium containing pronase or Tyrode at a final concentration of 0.5% [see; for example, D. M. Glover et al., Eds., DNA Cloning 4 Mammalian Systems A Practical Approach 2nd Ed. (1995)], and incubated at 37° C. for ten minutes. Blastocysts still covered with the zona pellucida were treated with pronase at 37° C. for five minutes. After confirming that the zona pellucida was removed, the blastocysts thus obtained were washed twice with PBS.

Then, a rabbit anti-cynomolgus monkey lymphocyte antiserum was diluted 20 times with M16 culture medium [see "DNA Cloning 4 Mammalian Systems A Practical Approach" indicated above, and others]. Blastocysts were transferred into this diluted solution and incubated at 37° C. for 30 minutes. The blastocysts thus obtained were washed three times with PBS. The blastocysts were transferred into a solution of complement diluted 50 times with M16 culture medium and then incubated at 37° C. for 30 minutes. The blastocysts were then washed three times with PBS. When the trophectoderm was not completely removed from the blastocysts, it was removed mechanically using a glass needle under a microscope. Thus, the inner cell mass (ICM) was isolated by the procedure described above.

(3) Culture of Monkey Inner Cell Mass

MEM was removed from the 24-well culture dishes in which the feeder cells prepared in section (1) had been plated. An 800-μl aliquot of ES cell culture medium [ES cell culture medium: Table 3] was added to each well.

ICM prepared in section (2) was transferred into each well at a cell density of one cell/well using a micropipette, and the cells were incubated under 5% $CO_2$ at 37° C. for seven days. To avoid inhibition of ICM implantation, the medium was not changed for the first three days after the start of the culture, and the implantation was monitored every day under a microscope.

TABLE 3

COMPOSITION OF ES CELL CULTURE MEDIUM

| PRODUCT NAME | AMOUNT |
| --- | --- |
| DMEM/F12 (SIGMA) | 500 ml |
| FBS (JRH BIOSCIENCES) | 75 ml |
| GLUTAMINE (SIGMA; 200 mM) | 5 ml |
| PENICILLIN (SIGMA; 10.000 IU/ml) AND STREPTOMYCIN (SIGMA; 10 mg/ml) MIXTURE | 5 ml |
| SODIUM PYRUVATE (SIGMA; 100 mM) | 5 ml |
| SODIUM BICARBONATE (SIGMA; 7.5%) | 8 ml |
| 2-MERCAPTOETHANOL (SIGMA; FINAL CONCENTRATION $10^{-4}$ M) | 4 μl |
| LIF(ESGRO; FINAL CONCENTRATION 1000 U/ml) | 0.5 ml ($10^6$ U/ml) |

On day 7 of the culture, the ICM had dispersed into single cells. The ES cell culture medium was removed from each well, and the wells were washed once with PBS. 300 μl of a 0.25% trypsin/0.02% EDTA solution was added to each well, and then immediately removed. The 24-well culture dishes were then incubated at 37° C. for one minute. After cell dispersal was confirmed under a microscopes 500 μl of ES cell culture medium was added to each well. The cells were dispersed by thorough pipetting.

All of the cells described above were transferred into the wells of fresh 24-well culture dishes in which feeder cells had been plated in advance. 300 μl of ES cell culture medium was added to each well, and thus each well contained 800 μl of culture medium in total. Then, the medium was thoroughly mixed to plate the cells evenly. The ES cell culture medium was changed once every two days. Cell populations presumed to comprise ES cells grew in less than seven days following cell dispersion, and were observed every day for the appearance of colonies. When an ES cell colony appeared, the cells in that 24-well culture plate were trypsinized, and then further subcultured. During this period, the ES cell culture medium was changed every day or once every two days. As a result, a number of ES cell lines were yielded from the blastocysts of cynomolgus monkeys.

(4) Assessment of Simian ES Cells

Karyotype

The number of chromosomes in the ES cells were examined to determine if they were normal (the number of chromosomes was the same as for the monkeys from which the ES cells were obtained: 2n=42). The results showed that the established ES cell strains were of normal karyotype.

Pluripotency $1 \times 10^6$ cynomolgus monkey ES cells were given to an 8-week old SCID mouse by subcutaneous injection in the groin region. The formation of a tumor was observed 5 to 12 weeks after the injection. The tumor was fixed with Bouin's fixative or paraformaldehyde solution, and sliced into sections. The sections were stained with hematoxylin and eosin (HE stain), or immuno-stained for histological examination. Since there were very few monkey tissue-specific antibodies available for the immuno-staining, antibodies against human neuron-specific enolase (NSE), glia fibrillary acidic protein (GFAP), S-100 protein, and desmin were used.

The tumors were revealed to be teratomas comprising cell types derived from the ectoderm (neurons and glia), mesoderm (muscle, cartilage, and bone), and endoderm (ciliated epithelium and intestinal epithelium). In the immunohistological examination, neurons were detected using an antibody against NSE; glia were detected using antibodies against NSE and GFAP; peripheral neurons were detected using an antibody against NSE; cartilage was detected using an antibody against S-100 protein; and muscle was detected using an antibody against desmin. The findings described above show that the cynomolgus monkey ES cells have pluripotency (tridermic differentiation potency).

Morphological Features

1. The ES cells were characterized by a high nucleus/cytoplasm ratio, notable nucleolar and colony formations. 2. The colony was flatter in shape than the mouse ES cells.

Expression of Cell Surface Markers

To test the presence of stage-specific embryonic antigens (SSEA) which are cells surface markers used to characterize ES cells, the ES cells were immuno-stained using antibodies against the respective cell surface markers for SSEA-1 (negative control), SSEA-3, and SSEA-4. These antibodies are available from "The Developmental Studies Hybridoma Bank of the National Institute of Child Health and Human Development". The ES cells were assessed for each SSEA cell surface marker using the procedure described below: The cells were fixed with 4% paraformaldehyde and incubated with a primary antibody. The cells were then incubated with a labeled polymer (Simple Stain PO, Nichirei) comprising an amino acid polymer conjugated with peroxidase and a secondary antibody. Detection was carried out by adding Simple Stain DAB solution (Nichirei). While SSEA-1 was undetectable, SSEA-3 and SSEA-4 were detected.

Alkaline Phosphatase Activity

Alkaline phosphatase activity was assayed using HNPP (Roche) and Fast-Red TR SaH as a substrate. Alkaline phosphatase was detected.

EXAMPLE 7

Culture of Simian ES Cells (A) Preparation of Feeder Cells

In the same way as described above in Example 6, MEF cells were obtained from 12.5 day-old mouse embryos and cultured in MEM containing 10% FBS and from the first to the third generation until confluent. To inactivate cell division, MEF cells were cultured for two or three hours in MEM containing MMC at a final concentration of 10 μg/ml. Then, the culture medium containing MMC was removed and the cells were washed three times with PBS. The cells were harvested by trypsinization (0.05% trypsin/1 mM EDTA), and the cell count was determined.

MMC-treated $2 \times 10^4$ MEF cells were plated in each well of 24-well gelatin-coated culture dishes.

(B) Culture of Simian ES Cells (CMK-1 Strain)

An ES cell culture medium was prepared according to the procedure described in Example 6. CMK-1 strain ES cells (hereinafter also referred to as "CMK-1") were plated on feeder cells prepared by the procedure described above in section (A). At this point, the ES cells were not dispersed into single cells but plated as cell masses of 5 to 10 cells. The culture medium was changed daily or every two days. The cells were passaged every 4 to 6 days.

On passaging, the cells were washed once with PBS, and 0.25% trypsin/PBS or 0.1% collagenase/DMEM was added to the cells, followed by incubation 37° C. for two to ten minutes. The cells were suspended in ES cell culture medium, and centrifuged at 1000 rpm for five minutes. The cells were then plated on freshly prepared feeder cells at a cell ratio of 1:2 to 1:4. A commercially available solution for cell cryopreservation, or 10 to 20% DMSO/DMEM was used to store the cells.

EXAMPLE 8

Gene Transfer Experiments Using Simian ES Cells (CMK-1 Strain)

<Gene Transfer into Simian ES Cells (CMK-1 Strain)>

A gene was introduced into simian ES cells using the VSV-G-pseudotyped SIV vector [self-inactivating (SIN) vector] for EGFP expression (FIG. 4) prepared by the procedure described above. The functional titer of the vector solution was $1.9 \times 10^9$/ml.

On the day before gene transfer, at a cell density of $7.5 \times 10^4$ cells/ml, CMK-1 cells were plated on to feeder cells ($2.5 \times 10^5$ cells/ml) On the day of gene transfer (Day 0), the SIV vector described above was diluted with the ES cell culture medium (Example 6) to adjust the MOI to 1, 10, and 100, based on the cells prepared as described above. Polybrene was added at a concentration of 8 μg/ml, and transduction was carried out once. The medium was changed after ten hours. From the next day (Day 1), the cells were passaged on to feeder cells every five to six days at a cell ratio of 1:3 to 1:4.

The efficiency of gene transfer into ES cells (CMK-1 strain) was determined according to the formula below, which is based on the EGFP expression level as estimated by FACScan. Since the CMK-1 cells were cultured on feeder cells, samples recovered using trypsin contained both CMK-1 and feeder cells. In addition, the SIV vector can deliver genes into mitomycin C-treated feeder cells as well as into CMK-1 cells. Therefore cells expressing EGFP included both CMK-1 and feeder cells. EGFP expression level was determined only in CMK-1 cells and according to the procedures described below in sections "(A) Assay for the expression level of EGFP in feeder cells" and "(B) Determination of cell ratio of CMK-1 and feeder cells" using the normalization equation described below.

<Normalization Equation for the Efficiency of Gene Transfer for CMK-1>

In each FACS sample, EGFP expression level in CMK-1 cells is represented by Ec; EGFP expression level in feeder cells is represented by Ef; and EGFP expression level in the mixture of CMK-1 and feeder cells is represented by Eb. If c denotes the number of CMK-1 cells and f denotes the number of feeder cells:

$$f \cdot Ef + c \cdot Ec = (f+c)Eb$$

A rearrangement of the formula gives the following equation:

$$Ec = \{(f+c)Eb - f \cdot Ef\}/c$$

Assuming $c/(f+c) = k$ yields:

$$1/k = 1 + f/c$$

Substituting this equation in the above equation yields the following:

$$EC = Eb/k - (1/k - 1)/Ef$$
$$= (Eb - Ef)/k + Ef$$

This gives the equation shown below:

$$\text{mean } Ec = \{(Eb-Ef)/n \cdot , 1/k_i\} + Ef$$

$$\begin{aligned}\text{Standard error } SEM \\ \text{(srandard error of means)}\end{aligned} = 1/n \cdot (_n(Ec_i - \text{mean})^2)^{1/2}$$

$$= (Eb - Ef) \cdot (_n(1/k_i - 1/n_n 1/k_i)^2)^{1/2}$$

Thus, the normalization equation described above is reached.

(A) Assay for EGFP Expression in Feeder Cells

The SIV vector was only introduced into feeder cells, and at MOI=1, 10, and 100. The cells were passaged and FACS analysis was carried out by the same procedures as described above.

(B) Determination of the Cell Ratio for CMK-1 and Feeder Cells

CMK-1 cells were distinguished from feeder cells using the method described below. The anti-HLA-ABC antibody, which is an antibody against human HLA (mouse anti Human HLA-ABC: RPE, Serotec Ltd.), does not react to mouse-derived feeder cells, but does react to cynomolgus monkey-derived CMK-1 cells. This antibody was allowed to react with a suspension of CMK-1 and feeder cells, and the ratio between CMK-1 and feeder cells was determined by FACS.

Figure 5:
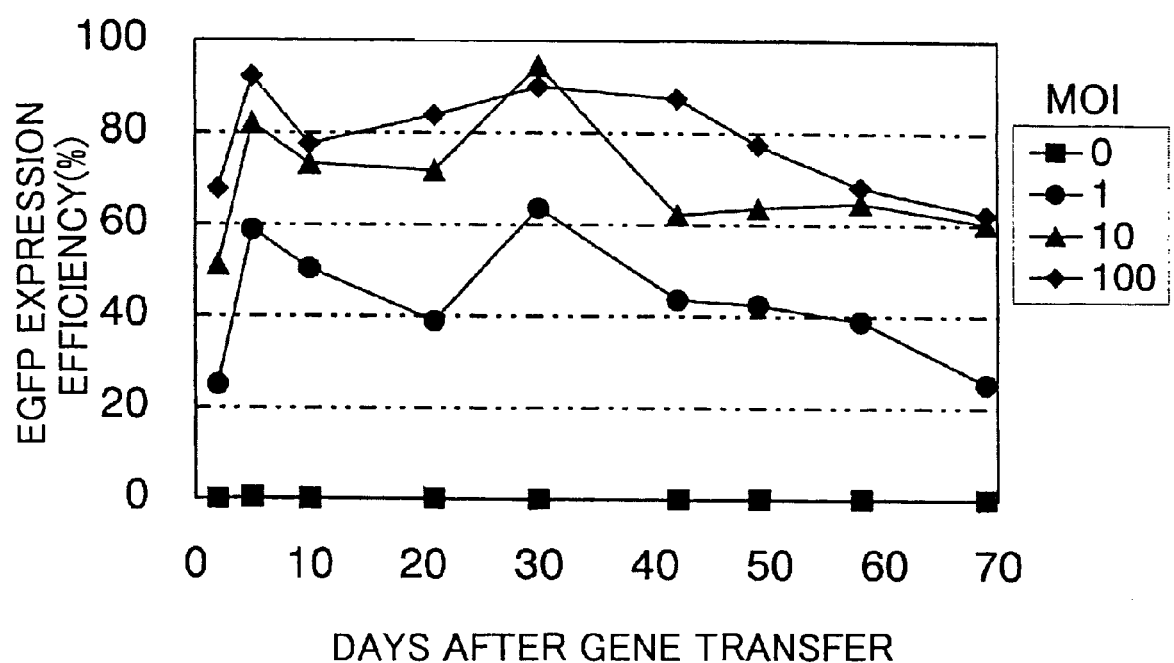
FIG. 5 is a diagram showing the time course of EGFP expression in CMK-1 strain ES cells in which the EGFP gene had been introduced using the SIV vector. The horizontal axis indicates the number of days after gene transfer (day 0). The vertical axis indicates the percentage of EGFP-expressing CMK-1 cells. Values for the efficiency of CMK-1 gene transfer have been corrected for the contribution of feeder cell contamination, using the method indicated in the Examples: "normalization equation for the efficiency of gene transfer for CMK-1". The efficiency of gene transfer was dependent on MOI and was exceedingly high two days after gene transfer; at MOI=100 the efficiency was 90% or higher; at MOI=10 it was about 80%; and at MOI=1 it was about 60%. This high transgenic efficiency lasted for at least about two months.
Figure 6:
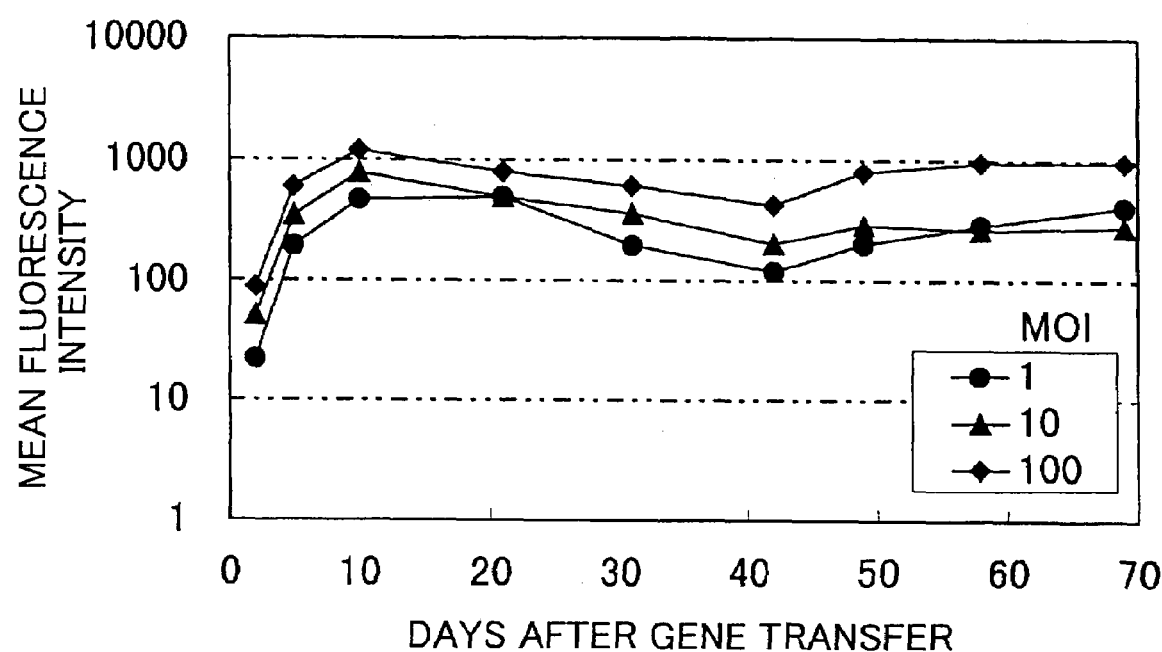
FIG. 6 is a diagram showing the time course of mean EGFP fluorescence intensity in CMK-1 strain ES cells into which the EGFP gene had been introduced via the SIV vector. The horizontal axis indicates the number of days after gene transfer (day 0). The vertical axis indicates mean EGFP fluorescence intensity obtained by FACS analysis. The mean fluorescence intensity of EGFP-expressing cells was hardly reduced over about two months.
Figure 7:
FIG. 7 shows micrographs of fluorescent images of EGFP expression in CMK-1 strain ES cells into which a gene had been introduced using the SIV vector.
Figure 7:
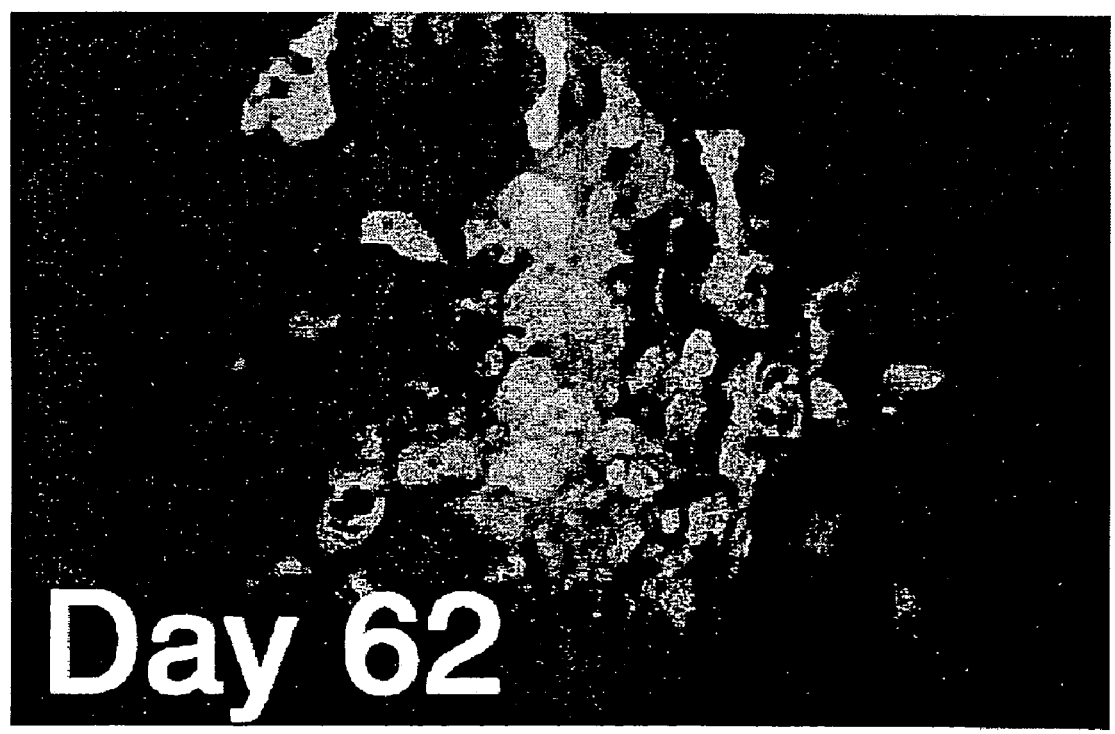

The efficiency of SIV vector-mediated gene transfer into simian ES cells was determined (FIG. 5). The efficiency of gene transfer into CMK-1 cells was corrected to eliminate the contribution of feeder cell contamination, using the method described above in the section "normalization equation for the efficiency of gene transfer for CMK-1". The efficiency of gene transfer was dependent on MOI and was exceedingly high two days after gene transfer. At MOI=100 the efficiency was 90% or higher; at MOI=10 it was about 80%; and at MOI=1 it was about 60%. This high transgenic efficiency lasted for at least about two months. A time course of mean fluorescence intensity was determined in CMK-1 cells into which the EGFP gene had been introduced. The mean fluorescence intensity of EGFP-expressing cells was hardly reduced over about two months (FIG. 6). Micrographs for the CMK-1 cells ("green" ES cells) in which the EGFP gene had been introduced via the SIV vector are shown in FIG. 7.

EXAMPLE 9

Efficiency of SIV Vector-Mediated Gene Transfer into Simian ES Cells and Murine ES Cells To test whether the efficiency of SIV vector-mediated gene transfer depends on the species from which the ES cells were derived, genes were introduced into murine ES cells (D3 strain) by the same method as described in Example 8.

On the day before gene transfer, CMK-1 cells were plated at a cell density of $7.5 \times 10^4$ cells/ml on to feeder cells ($2.5 \times 10^5$ cells/ml) On the day of gene transfer (Day 0), the above-described VSV-G-pseudotyped SIV vector [self-inactivating (SIN) vector] for EGFP expression (FIG. 4) was diluted with the ES cell culture medium (Example 6) to adjust the MOI to 1, 10, and 100, based on the cells prepared as described above. Polybrene was added at a concentration of 8 μg/ml, and transduction was carried out once. The medium was changed after ten hours. From the next day (Day 1), the cells were passaged. on to feeder cells every five to six days at a cell ratio of 1:3 to 1:4. On the day before gene transfer, murine ES cells (D3 strain) were plated at a cell density of $1 \times 10^5$ cells/ml and on nearly the same number of feeder cells. The same type of feeder cell as for CMK-1 was used. The day after the plating, the above-described SIV vector was added to the medium at MOI=10. Polybrene was added at a concentration of 8 μg/ml, and transduction was carried out once. From the next day (Day 1), the ES cells were passaged on feeder cells every other day. The cell ratio was 1:8 to 1:10.

The efficiency of gene transfer into each ES cell type at MOI=10 is shown in FIG. 8. The efficiency of gene transfer into simian ES cells was found to be higher than that into murine ES cells (FIG. 8). When an SIV-based vector is used, genes are thought to be introduced more efficiently into primate cells such as SIV's natural host monkey cells, than into cells from a different species such as mouse.

INDUSTRIAL APPLICABILITY

The VSV-G-pseudotyped simian immunodeficiency virus vector for gene transfer into primate ES cells of the present invention is useful for research into embryology and disease, clinical applications, and experimental models for primates including humans. Furthermore, the vector of the present invention enables screening for genes, reagents, and such, which control the specific differentiation of tissues or cells from ES cells. This screening method is highly advantageous in selecting genes, reagents, and the like, which are involved in the specific differentiation of tissues or cells, and which are useful in preparing desired differentiated cells or tissues.

The invention claimed is:

1. A method for introducing an isolated nucleic acid into a primate embryonic stem cell, which comprises the step of contacting a cultured primate embryonic stem (ES) cell with a recombinant simian immunodeficiency (rSIV) viral particle in vitro, wherein the rSIV particle is pseudotyped with VSV-G, wherein said isolated nucleic acid is packaged within the rSIV particle and the nucleic acid is of a size allowing packaging of said nucleic acid into said rSIV particle, thereby infecting the cultured primate ES cell with the rSIV particle and introducing the nucleic acid into the cultured primate ES cell wherein the nucleic acid is expressed in the cultured primate ES cell in vitro.

2. The method according to claim 1, wherein the rSIV particle is derived from an agm strain.

3. The method according to claim 1, wherein the rSIV particle is a self-inactivating viral particle.

4. The method according to claim 1, wherein the primate belongs to the Old World primates, of the family Cercopithecidac, genus *Macaca*.

5. A cultured primate embryonic stem cell generated by the method of claim 1.

6. The cultured primate embryonic stem cell according to claim 5, wherein the rSIV particle is derived from an agm strain.

7. The cultured primate embryonic stem cell according to claim 5, wherein the rSIV particle is a self-inactivating viral particle.

8. The cultured primate embryonic stem cell according to claim 5, wherein the primate belongs to the Old World primates, of the family Cercopithecidae, genus *Macaca*.

9. A method for determining the effect of an introduced isolated nucleic acid on the proliferation or differentiation of a cultured primate ES cell, which comprises the steps of:

(a) contacting a cultured primate embryonic stem (ES) cell with a recombinant simian immunodeficiency (rSIV) viral particle in vitro, wherein the rSIV particle is pseudotyped with VSV-G, wherein said isolated nucleic acid is packaged within the rSIV particle and the nucleic acid is of a size allowing packaging of said nucleic acid into said rSIV particle, thereby infecting the cultured primate ES cell with the rSIV particle and introducing the nucleic acid into the cultured primate ES cell wherein the nucleic acid is expressed in the cultured primate ES cell; and (b) determining the proliferation or differentiation of the cultured primate ES cell infected with said rSIV particle in vitro.

10. The method according to claim 9, wherein the rSIV particle is derived from an agm strain.

11. The method according to claim 9, wherein the rSIV particle is a self-inactivating viral particle.

12. The method according to claim 9, wherein the primate belongs to the Old World primates, of the family Cercopithecidae, genus *Macaca*.

* * * * *

UNITED STATES PATENT AND TRADEMARK OFFICE
CERTIFICATE OF CORRECTION

| | |
|---|---|
| PATENT NO. | : 7,323,337 B2 |
| APPLICATION NO. | : 10/479912 |
| DATED | : January 29, 2008 |
| INVENTOR(S) | : Yutaka Hanazono et al. |

Page 1 of 1

It is certified that error appears in the above-identified patent and that said Letters Patent is hereby corrected as shown below:

At column 43, lines 42-43, in claim 4, replace the word "Cercopithecidac" with --Cercopithecidae--.

Signed and Sealed this

Thirteenth Day of May, 2008

JON W. DUDAS
*Director of the United States Patent and Trademark Office*

SEQUENCE LISTING

<160> NUMBER OF SEQ ID NOS: 40

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 1
gcagatctca accaggaggc gaggctgcat tttggg                                 36

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 2
gcgaattcta cttactggtg ctgtaaagga gccaaa                                 36

<210> SEQ ID NO 3
<211> LENGTH: 40

```
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 3
atcggaattc ttttattgta agatggattg gtttttaaat                              40

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 4
cgggatccgc ggccgcggat atggatctgt ggagatagag gaacatat                    48

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 5
tcgagactag tgacttggtg agtaggctt                                          29

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 6
tcgaaagcct actcaccaag tcactactc                                          29

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:
      artificially Synthesized Oligonucleotide Sequence

<400> SEQUENCE: 7
aatttctcga gcggccgca                                                     19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence:
      artificially Synthesized Oligonucleotide Sequence

<400> SEQUENCE: 8
aatttgcggc cgctcgaga                                                     19

<210> SEQ ID NO 9
<211> LENGTH: 35
<212> TYPE: DNA
```

<213> ORGANISM: Artificial Sequence
<220> FEATURE:
<223> OTHER INFORMATION: Description of Artificial Sequence:
      artificially Synthesized Primer Sequence

<400> SEQUENCE: 9
gcggtacctg gatgggattt attactccga tagga                      35

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 10
gcgaattcga tagggcttga aacatgggta ctatttctgc                 40

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 11
gcgaattccc gtttgtgcta gggttcttag gcttct                     36

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 12
tccccgcgga tatggatctg tggagataga ggaacatatc                 40

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 13
gcgcggccgc ggatccgtcg acgcactttt taaaagaaaa ggga            44

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 14
gcgagctcta atgcaggcaa gtttattagc tttcta                     36

<210> SEQ ID NO 15
<211> LENGTH: 40
<212> TYPE: DNA
<213> ORGANISM: Artificial Sequence

```
<220> FEATURE:
<223> OTHER INFORMATION: Description of Artificial Sequence:
      artificially Synthesized Primer Sequence

<400> SEQUENCE: 15
ggaattcccg cggtagttat taatagtaat caattacggg                               40

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 16
cgggatccgc ggccgcttac ttgtacagct cgtccatgcc                               40

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 17
atcggaattc ttttattgta agatggattg gttttttaaat                              40

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 18
ataagaatgc ggccgctagc taagctgaat gaggagggtc aggcaactgt                    50

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 19
gcgaattccc gtttgtgcta gggttcttag gcttct                                   36

<210> SEQ ID NO 20
<211> LENGTH: 48
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 20
agctagctag gctagcggat atggatctgt ggagatagag gaacatat                      48

<210> SEQ ID NO 21
<211> LENGTH: 39
<212> TYPE: DNA
<213> ORGANISM: Artificial Sequence
<220> FEATURE:
```

<223> OTHER INFORMATION: Description of Artificial Sequence:
    artificially Synthesized Primer Sequence

<400> SEQUENCE: 21
tatataagca gagctcgctg gcttgtaact cagtctctt                    39

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence:
    artificially Synthesized Primer Sequence

<400> SEQUENCE: 22
tatataagtg cagtacgctg gcttgtaact cagtctctta                   40

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence:
    artificially Synthesized Primer Sequence

<400> SEQUENCE: 23
tataaaaagc gaagccgctg gcttgtaact cagtctctta                   40

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence:
    artificially Synthesized Primer Sequence

<400> SEQUENCE: 24
gcgaattcga tagggcttga aacatgggta ctatttctgc                   40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence:
    artificially Synthesized Primer Sequence

<400> SEQUENCE: 25
cggggtacct caatattggc cattagccat attattcatt                   40

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence:
    artificially Synthesized Primer Sequence

<400> SEQUENCE: 26
agttacaagc cagcgagctc tgcttatata gacctcccac                   40

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence:

-continued artificially Synthesized Primer Sequence

<400> SEQUENCE: 27
gcggtaccta gttattaata gtaatcaatt acggg             35

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 28
agttacaagc cagcgagctc tgcttatata gacctcccac        40

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 29
gcggtaccag gctccccagc aggcagaagt atgca             35

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 30
agttacaagc cagcgtactg cacttatata cggttctccc        40

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 31
ggggtaccat tgattattga ctagttatta atagtaatca        40

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 32
agttacaagc cagcggcttc gcttttata gggccgccgc         40

<210> SEQ ID NO 33
<211> LENGTH: 99
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 33
atgcgagctc gtcgacgcac tttttaaaag aaaagggagg actggatggg atttattact    60
ccgataggac gctggcttgt aactcagtct cttactagg                           99

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 34
gcgagctcta atgcaggcaa gtttattagc tttcta                              36

<210> SEQ ID NO 35
<211> LENGTH: 99
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 35
atgcgagctc gtcgacgcac tttttaaaag aaaagggagg actggatggg atttattact    60
ccgataggat caatattggc cattagccat attattcat                           99

<210> SEQ ID NO 36
<211> LENGTH: 99
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 36
atgcgagctc gtcgacgcac tttttaaaag aaaagggagg actggatggg atttattact    60
ccgataggaa ggctccccag caggcagaag tatgcaaag                           99

<210> SEQ ID NO 37
<211> LENGTH: 99
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 37
atgcgagctc gtcgacgcac tttttaaaag aaaagggagg actggatggg atttattact    60
ccgataggac attgattatt gactagttat taatagtaa                           99

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 38
gcgagctcta atgcaggcaa gtttattagc tttcta                              36

-continued

```
<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 39
atcggaattc ggccgccatg gtgagcaagg gcgaggagct                              40

<210> SEQ ID NO 40
<211> LENGTH: 40
<212> TYPE: DNA
<213> ORGANISM: Artificial Sequence
<220> FEATURE:
<223> OTHER INFORMATION: Description of Artificial Sequence:
      artificially Synthesized Primer Sequence

<400> SEQUENCE: 40
cgggatccgc ggccgcttac ttgtacagct cgtccatgcc                              40
```